(12) United States Patent
Hsu et al.

(10) Patent No.: US 9,085,543 B2
(45) Date of Patent: Jul. 21, 2015

(54) POLYMERIZABLE FULLERENE DERIVATIVE AND THEIR USE IN ORGANIC PHOTOVOLTAIC CELLS

(75) Inventors: Chain-Shu Hsu, Hsinchu (TW); Yen-Ju Cheng, Hsinchu (TW); Chao-Hsiang Hsieh, Hsinchu (TW); Pei-Jung Li, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 1140 days.

(21) Appl. No.: 13/046,462

(22) Filed: Mar. 11, 2011

(65) Prior Publication Data

US 2012/0060926 A1    Mar. 15, 2012

(30) Foreign Application Priority Data

Sep. 10, 2010 (TW) ................................ 99130938 A

(51) Int. Cl.
| | | |
|---|---|---|
| H01L 51/46 | (2006.01) | |
| C07C 69/616 | (2006.01) | |
| C07D 209/70 | (2006.01) | |
| C07D 231/54 | (2006.01) | |
| C07D 407/12 | (2006.01) | |
| C07D 305/06 | (2006.01) | |
| B82Y 10/00 | (2011.01) | |
| B82Y 20/00 | (2011.01) | |
| C07D 405/12 | (2006.01) | |
| C07D 405/14 | (2006.01) | |
| H01L 51/00 | (2006.01) | |
| H01L 51/42 | (2006.01) | |

(52) U.S. Cl.
CPC ............. *C07D 305/06* (2013.01); *B82Y 10/00* (2013.01); *B82Y 20/00* (2013.01); *C07C 69/616* (2013.01); *C07D 209/70* (2013.01); *C07D 231/54* (2013.01); *C07D 405/12* (2013.01); *C07D 405/14* (2013.01); *H01L 51/004* (2013.01); *H01L 51/0047* (2013.01); *C07C 2104/00* (2013.01); *H01L 51/0036* (2013.01); *H01L 51/4253* (2013.01); *Y02E 10/549* (2013.01)

(58) Field of Classification Search
USPC ........................................................ 136/263
See application file for complete search history.

(56) References Cited

U.S. PATENT DOCUMENTS

2005/0279399 A1 * 12/2005 Gaudiana et al. ............. 136/243
2010/0132782 A1 *  6/2010 Laird et al. .................... 136/256

OTHER PUBLICATIONS

Drees et al. Stabilization of the nanomorphology of polymer-fullerene "bulk heterojunction" blends using a novel polymerizable fullerene derivative. Journal of Materials Chemistry 2005, vol. 15, p. 5158-5163.*

(Continued)

*Primary Examiner* — Jeffrey T Barton
*Assistant Examiner* — Meisha Binkley
(74) *Attorney, Agent, or Firm* — WPAT, P.C.; Anthony King; Kay Yang

(57) ABSTRACT

The present invention discloses an inverted organic photovoltaic cell comprising a polymerizable fullerene interlayer adapted to enhance the device performance and lifetime. The polymerizable fullerene derivative comprises a fullerene core, a bridging functional group and a polymerizable functional group. The fullerene core can be either $C_{60}$ or $C_{70}$, and the bridging functional group comprises a cyclic hydrocarbon or a heterocyclic ring. The polymerizable functional group comprises a thermally polymerizable functional group or a photochemically polymerizable functional group.

2 Claims, 12 Drawing Sheets

| Metal electrode layer 60 |
|---|
| Hole-selective layer 50 |
| Active layer 40 |
| Thin film of the present invention 30 |
| Metal oxide layer 20 |
| Transparent conducting layer 10 |

(56) References Cited

OTHER PUBLICATIONS

Tollan et al. The synthesis of high-content fullerene functionalised polymers through the controlled addition of an amine-tagged fullerene derivative. New Journal of Chemistry 2008, vol. 32, p. 1373-1378.*

Huang et al. Enhancing performance of organic-inorganic hybrid solar cells using a fullerene interlayer from all-solution processing. Solar Energy Materials & Solar Cells 2010, vol. 94, p. 182-186.*

Padinger et al. Effects of Postproduction Treatment on Plastic Solar Cells. Advanced Functional Materials 2003, vol. 13, p. 85- 88.*

Cheng et al. Self-Assembled and Cross-Linked Fullerene Interlayer on Titanium Oxide for Highly Efficient Inverted Polymer Solar Cells. Chemistry of Materials 2011, vol. 23, p. 1512-1518.*

Kostyanovsky et al. Polymerizable fullerene-based material for organic solar cells. Thin Solid Films 2011, vol. 5149, p. 4119-4122.*

Steven K. Hau et al., Interfacial modification to improve inverted polymer solar cells, Journal of Materials Chemistry, 2008, pp. 5113-5119, vol. 18.

Steven K. Hau et al., High performance ambient processed inverted polymer solar cells through interfacial modification with a fullerene self-assembled monolayer, Applied Physics Letters, 2008, pp. 233304-1-233304-3, vol. 93.

Jing-Shun Huang et al., Enhancing performance of organic-inorganic hybrid solar cells using a fullerence interlayer from all-solution processing, Solar Energy Materials & Solar Cells, 2010, pp. 182-186, vol. 94.

M. S. White et al., Inverted bulk-heterojunction organic photovoltaic device using a solution-derived ZnO underlayer, Applied Physics Letters, 2006, pp. 143517-1-143517-3, vol. 89.

Highly Efficient and Stable Inverted Polymer Solar Cells Integrated with a Cross-Linked Fullerene Material as an Interlayer, J. Am. Chem. Soc., 2010, pp. 4887-4893, vol. 132, No. 13.

Yen-Ju Cheng et al., Combination of Indene-C60 Bis-Adduct and Cross-Linked Fullerene Interlayer Leading to Highly Efficient Inverted Polymer Solar Cells, J. Am. Chem. Soc., 2010, pp. 17381-17383, vol. 132, No. No. 49.

* cited by examiner

POLYMERIZABLE FULLERENE DERIVATIVE AND THEIR USE IN ORGANIC PHOTOVOLTAIC CELLS

FIELD OF THE INVENTION

The present invention relates to an inverted organic photovoltaic cell comprising a polymerizable fullerene interlayer made of polymerizable fullerene derivatives and adapted to enhance the device performance and lifetime.

BACKGROUND OF THE INVENTION

Although organic photovoltaic cells (OPVCs) fabricated from semiconducting polymer have been demonstrated with performance comparable to or in some cases even better than their inorganic counterparts, the typically short lifetime of the OPVCs must be overcome before the launch of the large scale organic photovoltaics will be realized.

Most conventional OPVCs are degraded when exposed to water vapor and/or oxygen in the air. The top electrode in conventional OPVCs is air sensitive and thereby become the central cause of the instability of OPVCs. To overcome this issue, a feasible strategy by means of reversing the polarity of the devices are therefore adopted, and thereby inverted OPVCs have been investigate recently. The inverted OPVCs have the anti-oxidant and high stability characteristics which outperform the conventional OPVCs. The anodes (i.e. top electrode) of the inverted organic OPVCs are made of metals with high work-function, and the cathodes of those are composed of metal oxide.

Although such inverted OPVCs are provided with better stability, the inefficient electronic coupling of the inorganic metal oxide layer, such as the zinc oxide layer or the titania layer, to the polymer active layer is detrimental to the electron extraction.

The electron collection mechanisms at metal oxide layer are relatively less studied and less understood. It is believed that the electron collection loss at the interfaces is also a major contributing factor to the low efficiency of current inverted OPVCs. Electrons can not be efficiently captured from the blending system by the metal oxide, causing a space-charge buildup and the photoelectric conversion efficiency of the inverted OPVCs generally is worse than the conventional OPVCs thereby.

The inefficient electronic coupling of the underlying metal oxide layer to the upper blend film can be overcome or at least altered to acceptable levels by several methods. Attempts to create a self-assembly monolayer of fullerene derivatives have been reported with promising results. However, the drawbacks for the self-assembly monolayer of the fullerene derivatives are incomplete coverage on the metal oxide layer and have the probable desorption during the follow-up process (Hau, S. K.; Yip, H.-L.; Acton, O.; Baek, N. S.; Ma, H.; Jen, A. K. Y. J. Mater. Chem. 2008, 18, 5113; and Hau, S. K.; Yip, H.-L.; Ma, H.; Jen, A. K. Y. Appl. Phys. Lett. 2008, 93, 233304/1).

In other literatures, the metal oxide nanotubes filled with fullerene derivatives are tried to be a selected layer to overcome the drawbacks of poor electron capture efficiency. However, based on the wet etching process, the mutual erosion between layers could not be prevented, such that for establishing the multilayer OPVCs with high efficiency, it is still unable to solve at the present stage (Huang, J.-S.; Chou, C.-Y.; Lin, C.-F. Sol. Energy Mater. Sol. Cells 2010, 94, 182).

Accordingly, it is an object of the present invention to provide an improved, high efficiency OPVCs.

Another object of the present invention is to provide an OPVC which reduces or eliminates losses found in prior art (White, M. S.; Olson, D. C.; Shaheen, S. E.; Kopidakis, N.; Ginley, D. S. Appl. Phys. Lett. 2006, 89, 143517/1).

SUMMARY OF THE INVENTION

In view of the aforementioned drawbacks in prior art, an object of the present invention is to provide an inverted organic photovoltaic cell comprising a polymerizable fullerene interlayer adapted to enhance the device performance by means of improving the electron extraction efficiency.

To achieve a goal of simple fabrication by all solution processing, a robust fullerene derivative interlayer is needed to prevent the subsequential wet etching processes when depositing the upper layer.

In one embodiment, the inverted OPVCs include a robust interlayer containing fullerene derivatives that can be processed from solution.

To achieve the above object, the inverted organic photovoltaic cell comprises an interlayer made of the polymerizable fullerene derivative as following description, and disposed between a metal oxide layer and an active layer.

The polymerizable fullerene derivatives comprise a fullerene core, a bridging functional group and a polymerizable functional group. The bridging functional group is connected between the fullerene core and the polymerizable functional group. The fullerene core comprises $C_{60}$ or $C_{70}$ fullerene, and the bridging functional group comprises cyclic hydrocarbon or a heterocyclic ring. The cyclic hydrocarbon or the heterocyclic ring may comprise a three-membered ring, a four-membered ring or a five-membered ring, and the heterocyclic ring further may comprise pyrazolo, pyrrolidine or isoxazole.

The polymerizable functional group of the polymerizable fullerene derivatives according to the present invention comprises a thermally polymerizable functional group or a photochemically polymerizable functional group. The thermally polymerizable functional group may be a styryl group, a vinyl group, benzocyclobutene, 1,2,2-trifluorovinyl ester or diacetylene. The photochemically polymerizable functional group may comprise oxetane.

Accordingly, the polymerizable fullerene derivatives and the inverted photovoltaic cells thereof according to the present invention provide one or more of the following advantages:

(1) Because the polymerizable fullerene derivatives of the present invention is highly amorphous after the polymerizable process and has high glass transition temperature (near 150° C.), the morphology of the polymerizable fullerene derivative interlayer of the present invention possesses highly thermal stability and do not easily become cluster or crystallite during the following thermal treatment.

(2) The inverted OPVCs comprises the interlayer made of the polymerizable fullerene derivatives of the present invention and used as an electron-selective layer, and thus the interlayer made of the polymerizable fullerene derivatives of the present invention can not only increase the electron capture efficiency but also be a hole blocking layer (HBL) so as to decrease the loss of electron/hole pairs in the vicinity of the interface of the active layer and the metal oxide layer and increase the photoelectric conversion efficiency.

(3) Since the interlayer made of the polymerizable fullerene derivatives of the present invention has the characteristic of hotspot passivation, the leakage current can be prevented.

(4) The interlayer made of the polymerizable fullerene derivatives of the present invention can form an additional p-n local heterojunction with electron donors in the active layer and practice ultra fast electron transfer more efficiently than the heterojunction formed in between the metal oxide and electron donors so as to increase the exciton dissociation efficiency.

(5) The interlayer formed by the polymerizable fullerene derivatives of the present invention can provide the nucleation site of the electron acceptor, which is [6,6]-phenyl-C61-butyric acid methyl ester (PCBM) and Indene-C60-bisadduct (ICBA), in the bulk heterojunction active layer to induce that the active layer generates the effective lateral microphase separation and simultaneously increase the crystallinity of electron donors.

(6) The interlayer made of the polymerizable fullerene derivatives of the present invention is an anti-etching and stable thin film, such that the interlayer of the present invention has solvent resistance property to resist the wet etching from the coating solvent during the subsequent procedure. The object of manufacturing organic photovoltaic cells via the wet process is achieved, and the manufacturing cost is effectively reduced.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
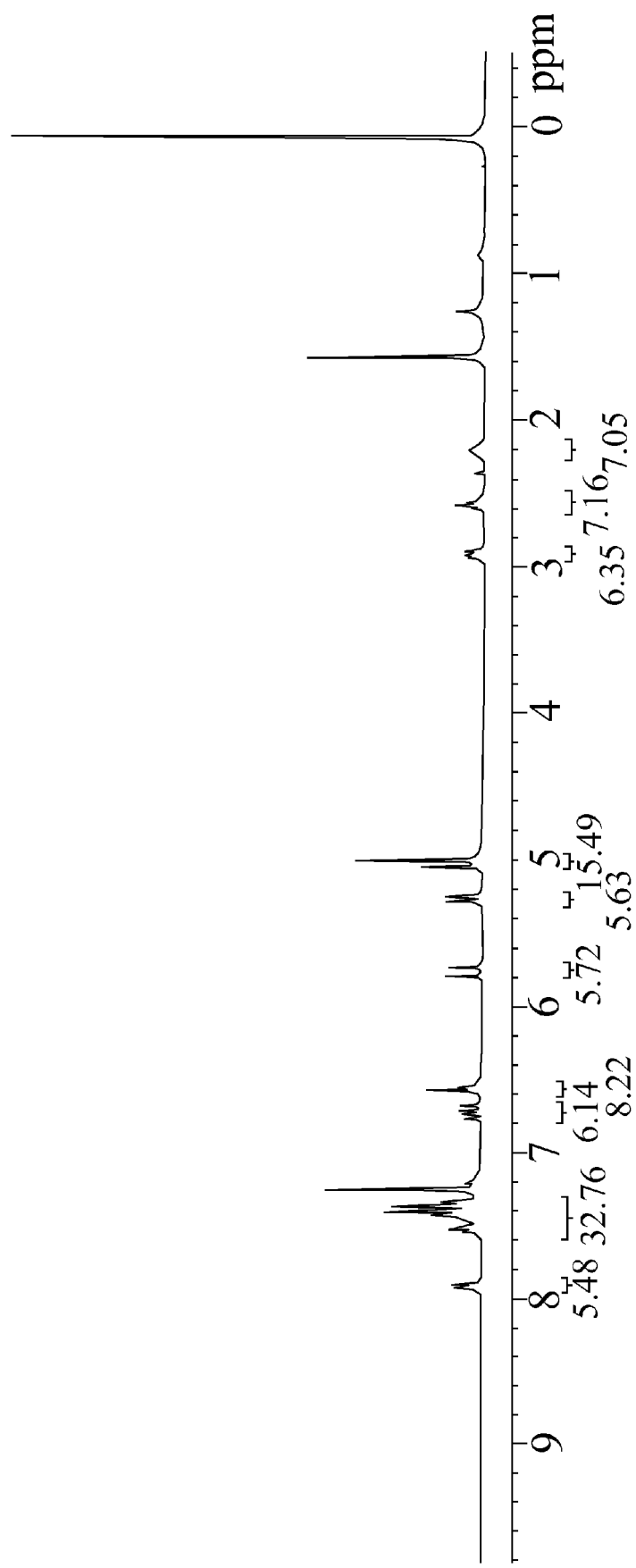
FIG. 1 is a $^1$H-NMR spectrum of $PC_{61}BSD$ of the present invention.

The present invention will now be described hereinafter with some preferred embodiments thereof with reference to the accompanying drawings. It is understood the experimental data shown in the embodiments are provided only for easy interpretation of the technical means of the present invention and should in no means be considered as restriction to the present invention. For instance, various embodiments are provided in the description in connection with different kinds of p-type polymers, i.e. poly(3-hexylthiophene) (P3HT) and poly[2,6-(4,4-bis(2-ethylhexyl)-4H-cyclopenta[2,1-b; 3,4-b']-alt-4,7-(2,1,3-benzothiadiazole)](PCPDTBT), and different n-type fullerene derivatives, i.e. PCBM and ICBA. It will be appreciated that the claimed invention may also be used with an active layer based on other photovoltaic materials.

The organic photovoltaic cell (OPVC) of the present invention comprises an interlayer made of the following polymerizable fullerene derivatives and disposed between a metal oxide layer and an active layer. The polymerizable fullerene derivatives of the present invention comprise a fullerene core, a bridging functional group and a polymerizable functional group. The bridging functional group is connected between the fullerene core and the polymerizable functional group. The fullerene core can be either $C_{60}$ or $C_{70}$ fullerene, and the bridging functional group comprises cyclic hydrocarbon or a heterocyclic ring. The cyclic hydrocarbon or the heterocyclic ring may comprise a three-membered ring, a four-membered ring or a five-membered ring, and the heterocyclic ring may comprise a three-membered heterocyclic ring, a four-membered heterocyclic ring or a five-membered heterocyclic ring. Additionally, the heterocyclic ring further may comprise pyrazolo, pyrrolidine or isoxazole.

The polymerizable functional group of the polymerizable fullerene derivatives according to the present invention comprises a thermally polymerizable functional group or a photochemically polymerizable functional group. The thermally polymerizable functional group may be a styryl group, a vinyl group, benzocyclobutene, 1,2,2-trifluorovinyl ester or diacetylene. The photochemically polymerizable functional group may comprise oxetane.

In addition, the polymerizable fullerene derivatives according to the present invention may comprise a spacer, and the spacer is connected to the bridging functional group and the polymerizable functional group. The spacer may be a phenyl group or butyric ester and it should not be limited thereon.

In an embodiment, when the polymerizable functional group is the thermally polymerizable functional group, the polymerizable fullerene derivatives represent as following formula (1) to formula (10), and however it should not be limited thereon.

(1)
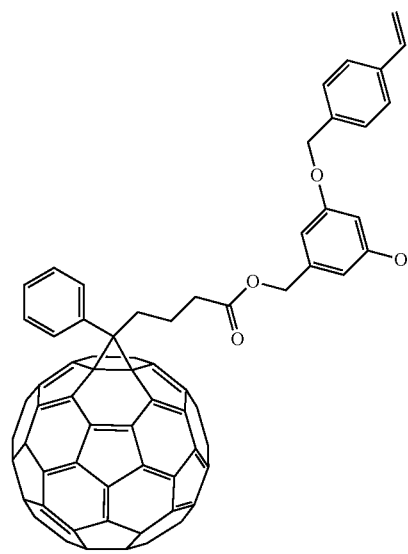
(2)
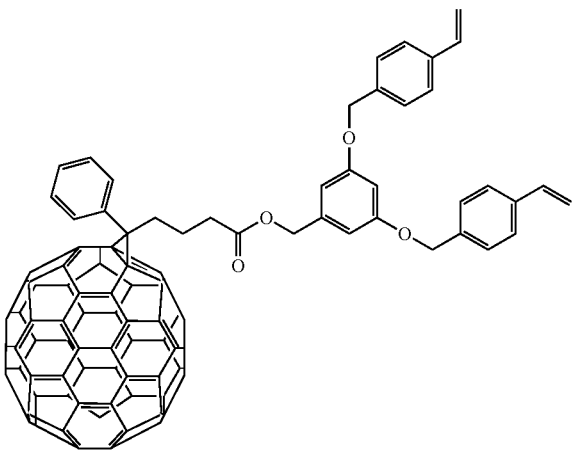
(3)
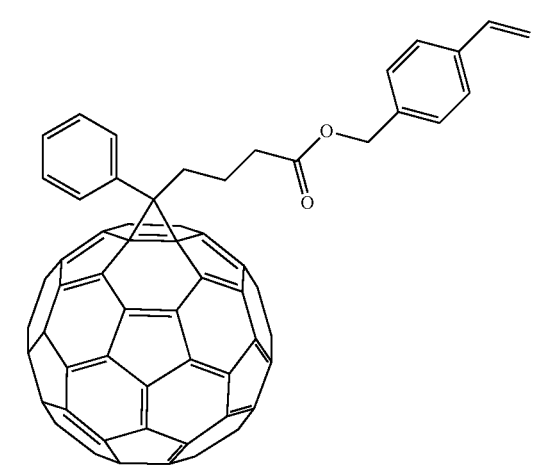
(4)
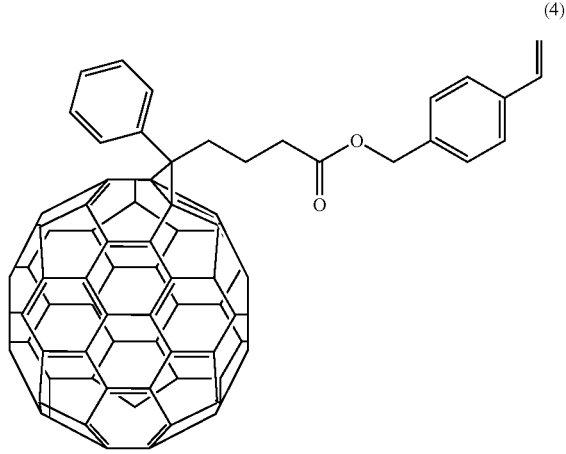
(5)
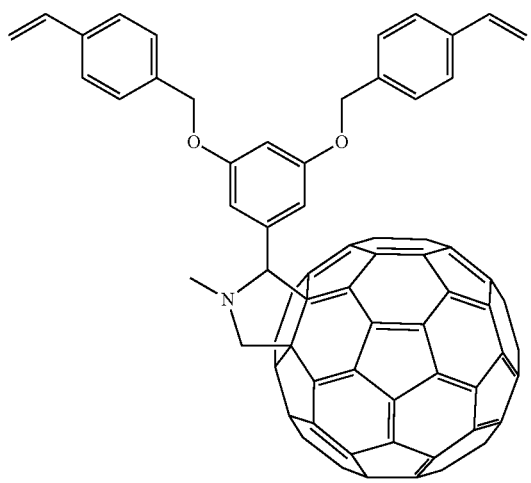
(6)
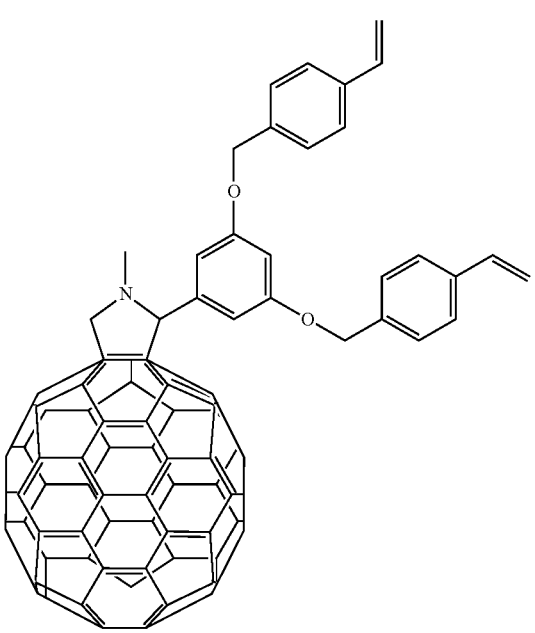

-continued

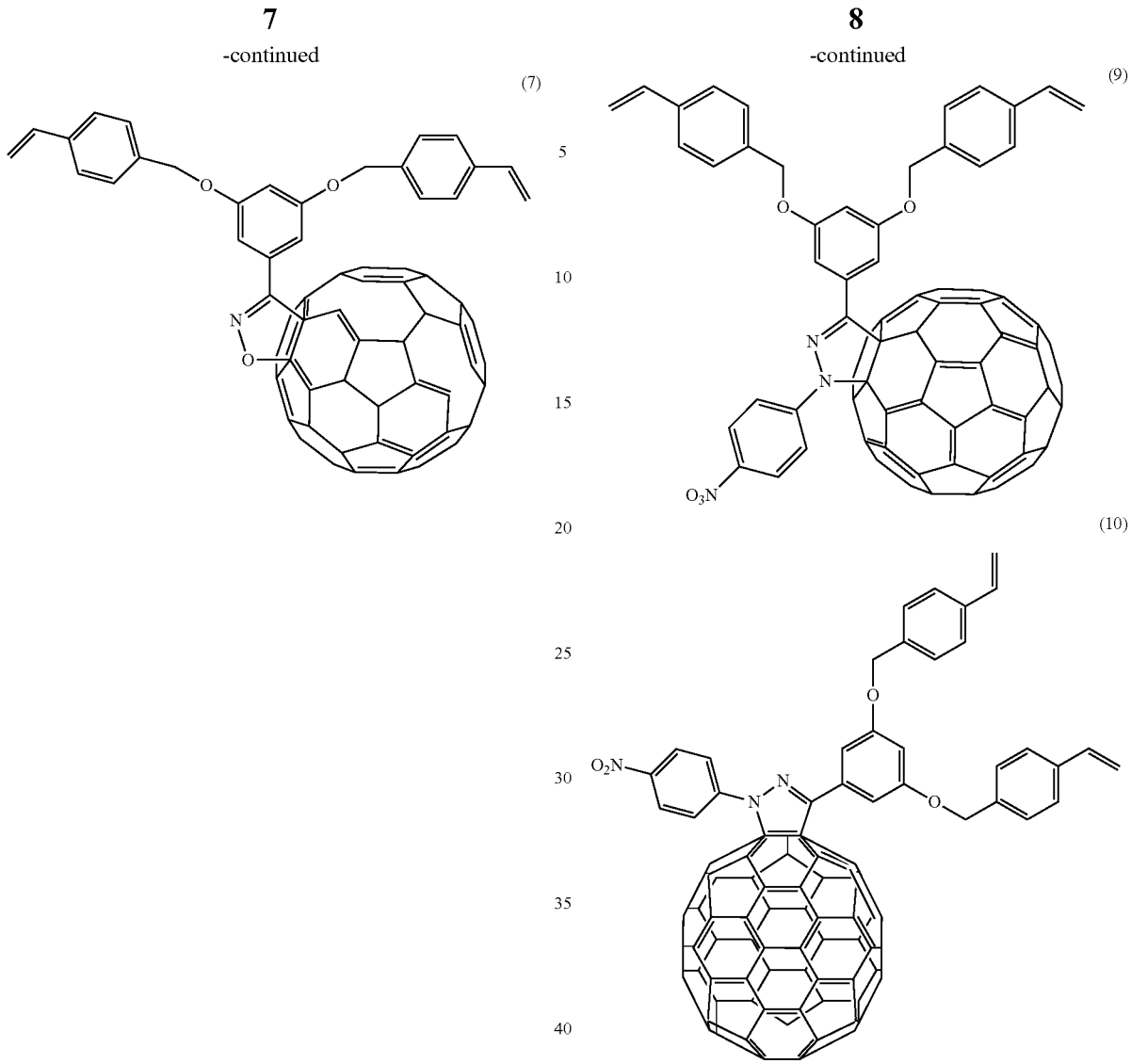

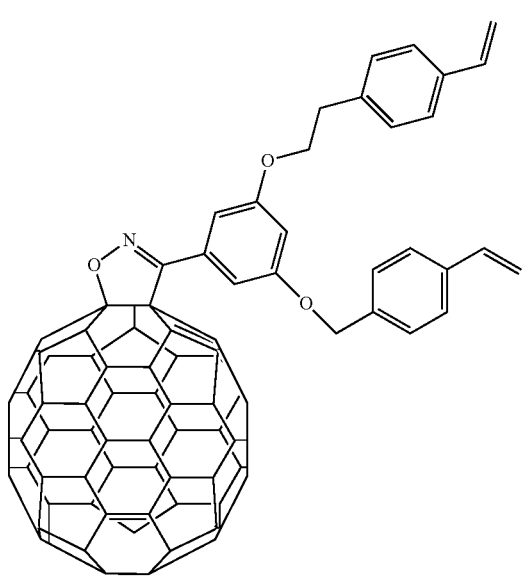

Wherein, the names of the formulas (1) to (10) are [6,6]-phenyl-$C_{61}$-butyric styryl dendron ester ($PC_{61}BSD$), [6,6]-phenyl-$C_{71}$-butyric styryl dendron ester ($PC_{71}BSD$), [6,6]-phenyl-$C_{61}$-butyric styrene ($PC_{61}BS$), [6,6]-phenyl-$C_{71}$-butyric styrene ($PC_{71}BS$), [60]-pyrrolidine styryl dendron fullerene ([60]-POSDF), [70]-pyrrolidine styryl dendron fullerene ([70]-POSDF), isoxazolo styryl dendron fullerene ([60]-ISDF), [70]-isoxazolo styryl dendron fullerene ([70]-ISDF), pyrazolo styryl dendron fullerene ([60]-PASDF) and [70]-pyrazolo styryl dendron fullerene ([70]-PASDF), respectively.

The bridging functional groups of the formulas (1) to (4) are the three-membered ring, and the bridging functional groups of the formulas (5) to (6), (7) to (8), and (9) to (10) are pyrrolidine, isoxazole and pyrazolo, respectively. Further, the polymerizable functional groups of the formulas (1), (2) and (5) to (10) are the cross-linkable functional group and are the two styryl groups represented in dendritic shape. The styryl functionality of the formulas (3) and (4) only allows linear polymerization rather than crosslinking.

Additionally, when the polymerizable functional group is the photochemically polymerizable functional group to perform cross-linking, the polymerizable fullerene derivatives represent as following formula (11) to formula (18), and however it should not be limited thereon.

(11)
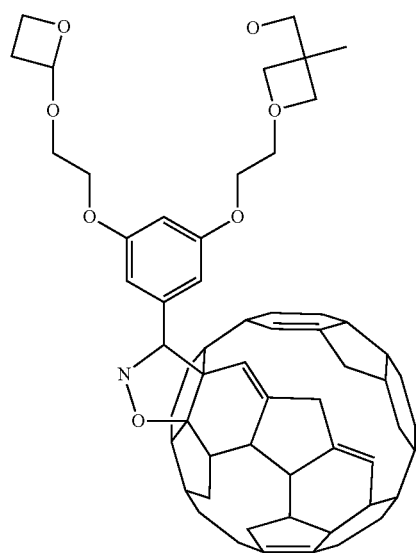
(12)
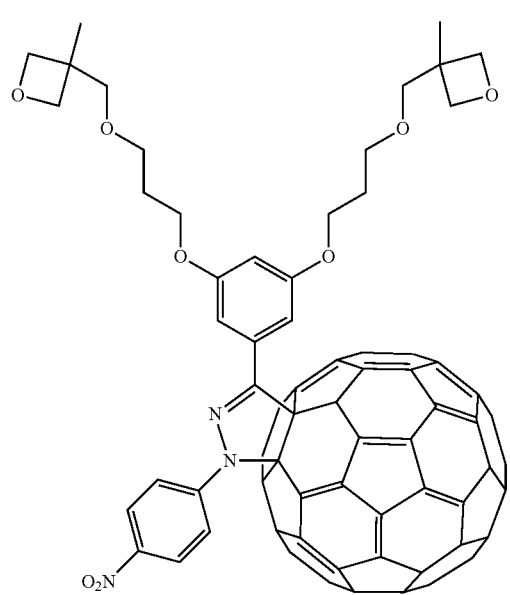

(13)
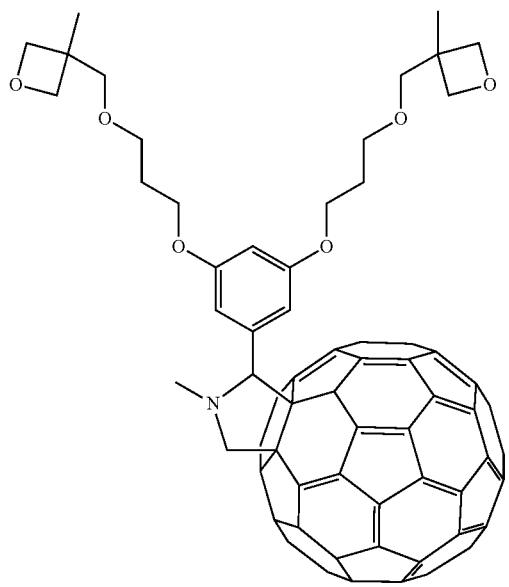
(14)
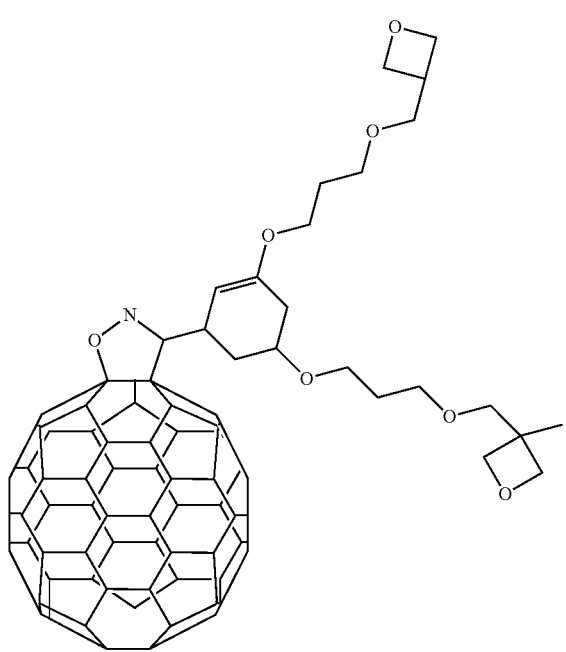

(15)
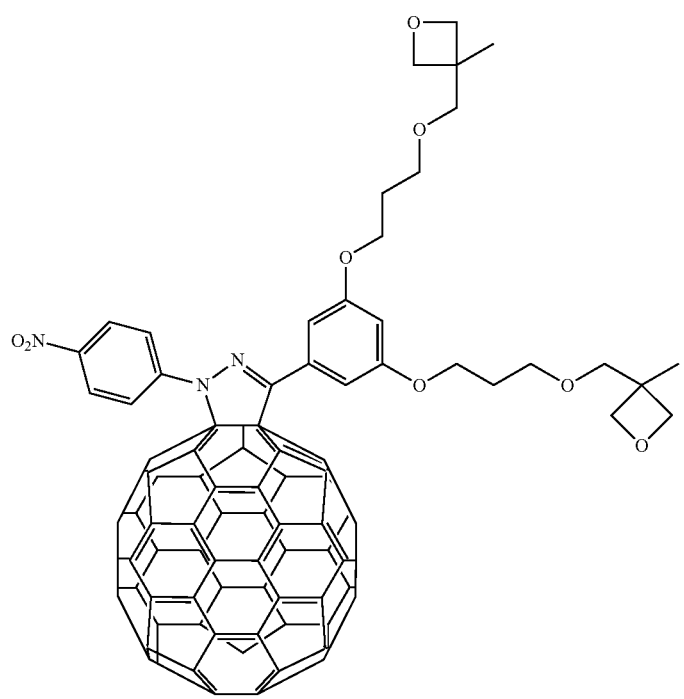
(16)
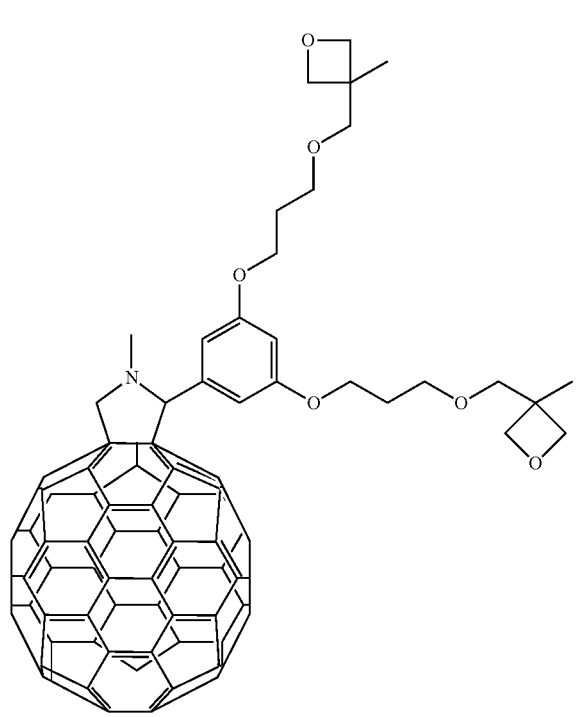

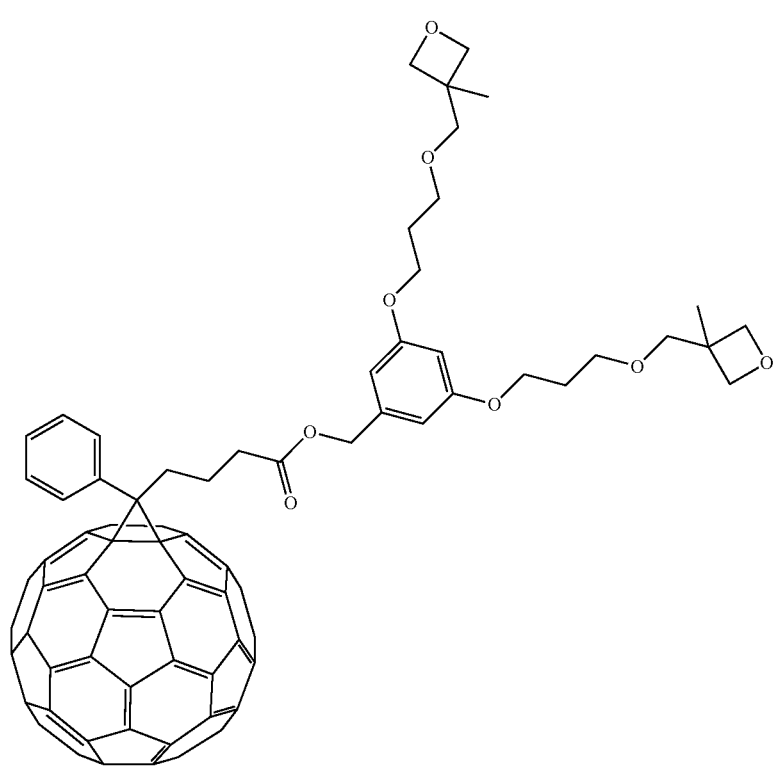

(17)

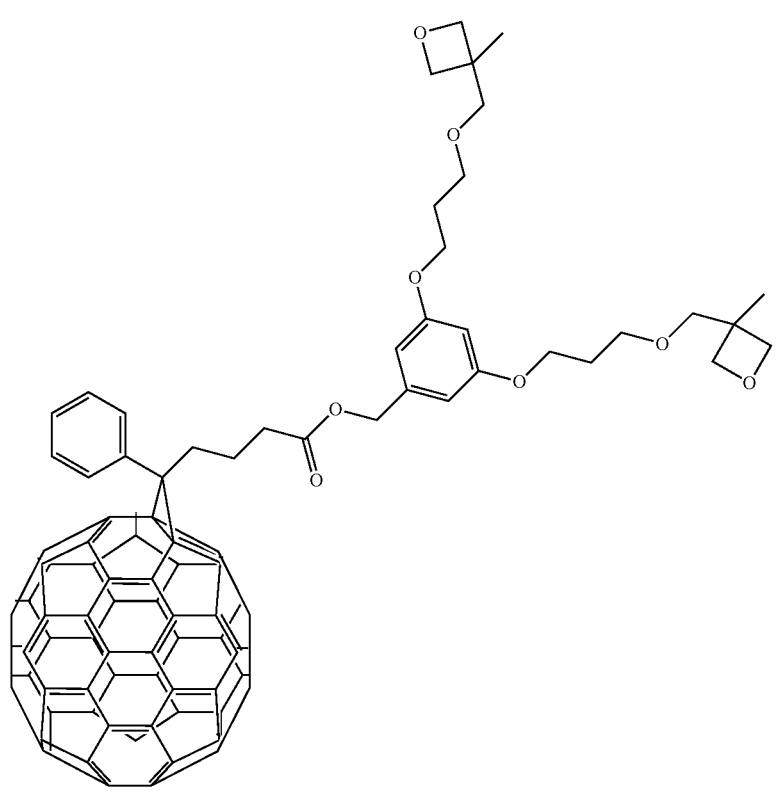

(18)

Wherein, the names of the formulas (11) to (18) are [60]-isoxazolo oxetane dendron fullerene ([60]-IODF), [60]-pyrazolo oxetane dendron fullerene ([60]-PAODF), [60]-pyrrolidine oxetane dendron fullerene ([60]-POODF), [70]-isoxazolo oxetane dendron fullerene ([70]-IODF), [70]-pyrazolo oxetane dendron fullerene ([70]-PAODF), [70]-pyrrolidine oxetane dendron fullerene ([70]-POODF), [6,6]-phenyl-$C_{61}$-butylic oxetane dendron ester ($PC_{61}BOD$) and [6,6]-phenyl-$C_{71}$-butylic oxetane dendron ester ($PC_{71}BOD$), respectively.

In a synthetic embodiment of the present invention, the above formulas (1) and (2) are used as examples, and the synthetic steps thereof are as follows.

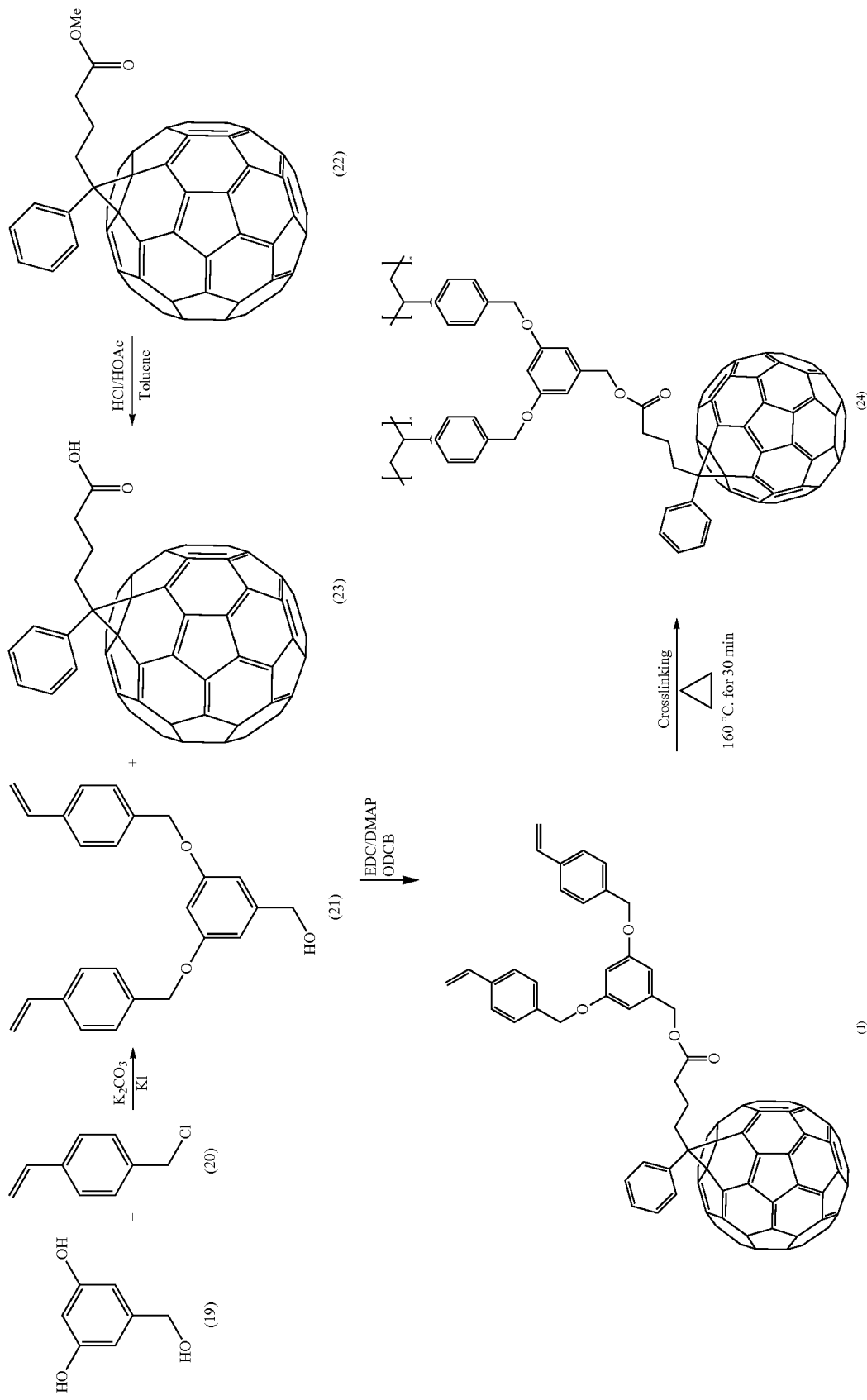

First, [6,6]-phenyl-$C_{61}$-butyric acid methyl ester (PCBM), formula (22), is hydrolyzed to obtain [6,6]-phenyl-$C_{61}$-butyric acid, PCBA representing formula (23). Further, styryl dendron (formula (21)) is obtained by the synthesis of 3,5-dihydroxybenzyl alcohol (formula (19)) and 4-vinylbenzyl chloride (formula (20)) under catalyzed by $K_2CO_3$ and KI. Sequentially, PCBA (formula (23)) is grafted to styryl dendron (formula (21)) by the esterification to obtain the fullerene derivative $PC_{61}BSD$ (formula (1)) of the present invention. Wherein, in the embodiment of the present invention, the interlayer as shown in formula (24) is obtained via heating $PC_{61}BSD$ at 160° C. for 30 min.

Furthermore, in the manufacturing method of $PC_{71}BSD$ (formula (2)), [6,6]-phenyl-$C_{71}$-butyric acid ($PC_{71}BA$) is obtained by the hydrolysis of [6,6]-phenyl-$C_{71}$-butyric acid methyl ester ($PC_{71}BM$). Other steps are the same as the above-mentioned steps of manufacturing $PC_{61}BSD$, and will not be repeated herein. When the polymerizable fullerene derivative is made by the photochemically polymerizable functional group, the formula (21) is replaced with oxethane, and following steps is the same as the steps of the polymerizable fullerene derivative made by the thermally polymerizable functional group and not repeated herein.

Figure 2:
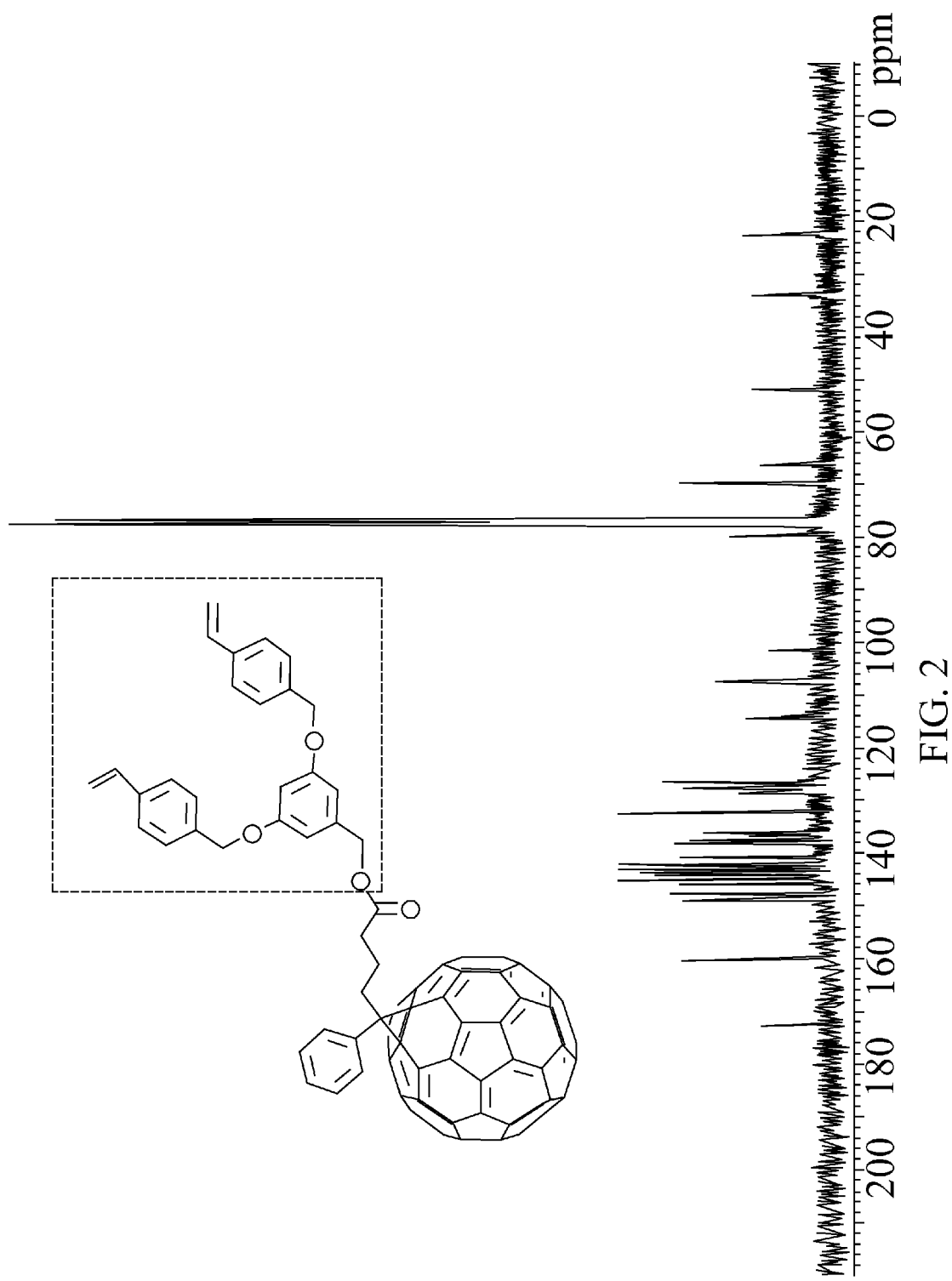
FIG. 2 a $^{13}$C-NMR spectrum spectrum of $PC_{61}BSD$ of the present invention.

In the present embodiment, the structure of $PC_{61}BSD$ is determined by $^1$H-nuclear magnetic resonance spectroscopy ($^1$H-NMR) and $^{13}$C-nuclear magnetic resonance spectroscopy ($^{13}$C-NMR), and the results thereof is shown as FIG. 1 and FIG. 2. As shown, $PC_{61}BSD$ is assuredly obtained by the foregoing steps of the manufacturing method.

Figure 3:
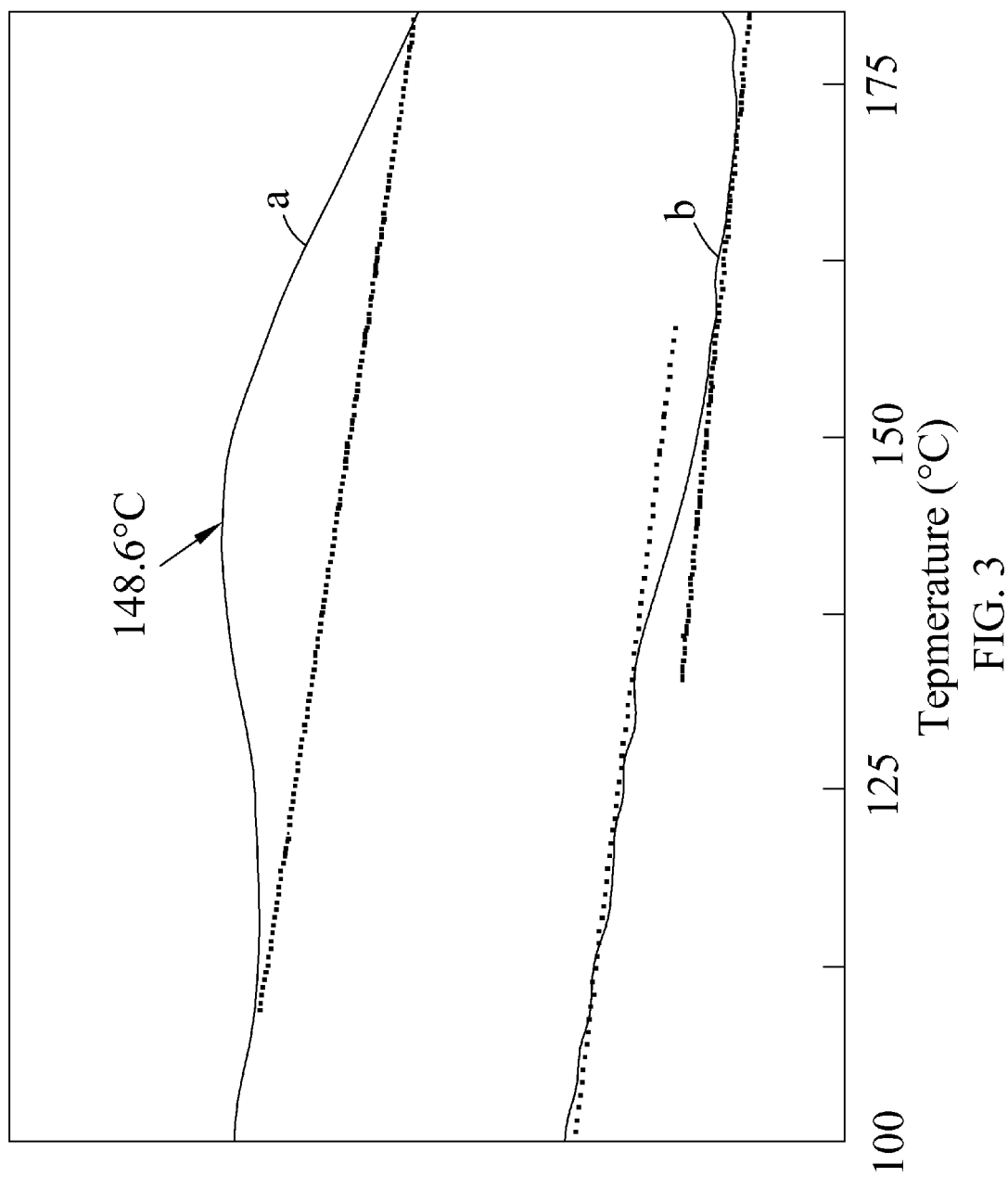
FIG. 3 is a graph illustrating $PC_{61}BSD$ of the present invention detected by the differential scanning calorimeter.

Additionally, the glass transition temperature (Tg) can be used as the criteria of determining the thermal property of $PC_{61}BSD$ then measured by the differential scanning calorimeter (DSC), as shown in FIG. 3. As shown, the curve a, which is the first heating scan, illustrates that the thermal cross-linking reaction is initiated under about 150° C., and then through the second heating scan (the curve b), $PC_{61}BSD$ of the present invention has high Tg (near 150° C.) to further determine that $PC_{61}BSD$ is amorphous. Thus, based on the high Tg, $PC_{61}BSD$ of the present invention has extremely high thermal stability.

Figure 4:
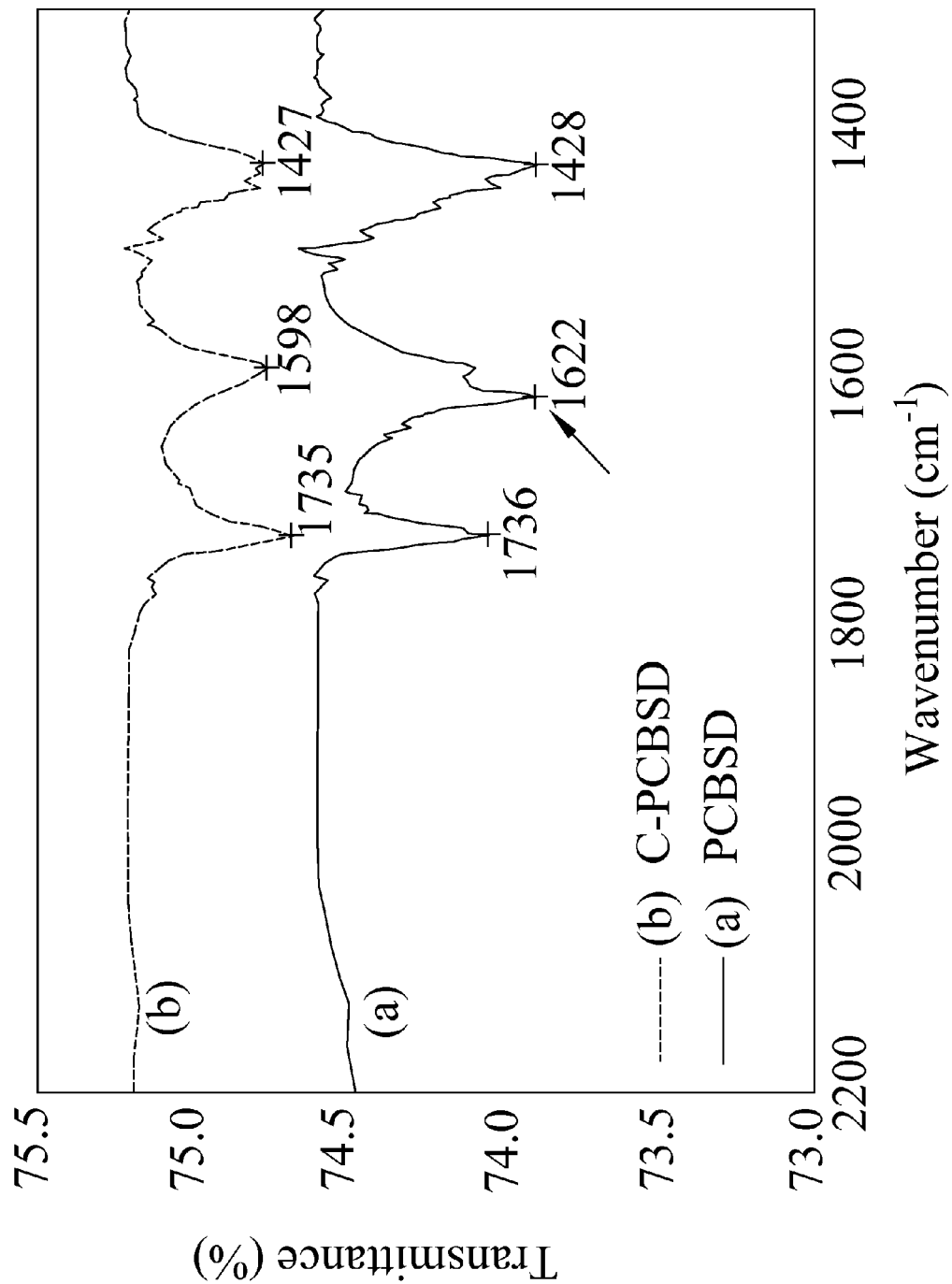
FIG. 4 is an infrared spectrum of $PC_{61}BSD$ of the present invention before and after the thermal treatment.

Infrared (IR) spectra are used to analyze whether $PC_{61}BSD$ of the present invention is processed to the thermal cross-linking reaction under the solid state thereof, and the results are shown in FIG. 4. As shown, the vibrational stretching of the vinyl group (C=C) at 1622 $cm^{-1}$ (labeled with an arrow) in the curve (a) completely disappears in the IR spectrum after the thermal treatment (curve (b)), undoubtedly proving the occurrence of cross-linking. The results reveal that the two arms of the dendron provide adequate flexibility for styryl groups to react in the solid state and to form the cross-linked $PC_{61}BSD$ interlayer.

Figure 5:
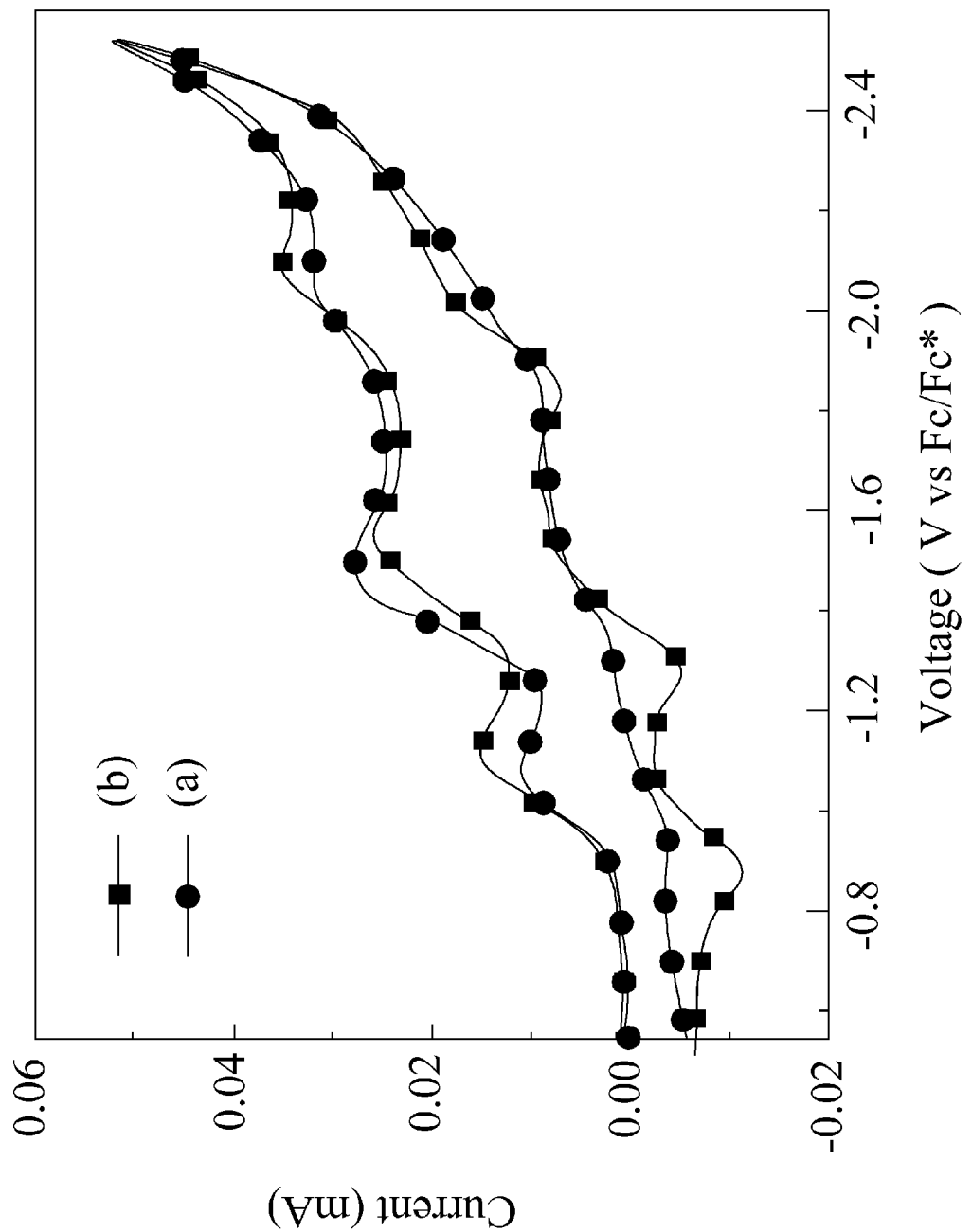
FIG. 5 is a graph illustrating the electrochemical characteristics of $PC_{61}BSD$ according to the present invention.

$PC_{61}BSD$ of the present invention still extends the electrochemical properties of PCBM, that is, the lowest unfilled molecular orbital (LUMO) of $PC_{61}BSD$ is very close to that of PCBM, as shown in FIG. 5. The curve (a) and (b) represent cyclic voltammogram of $PC_{61}BSD$ and PCBM, respectively. Thus, the $PC_{61}BSD$ interlayer of the present invention can be applicable to organic photovoltaic cells.

Figure 6:
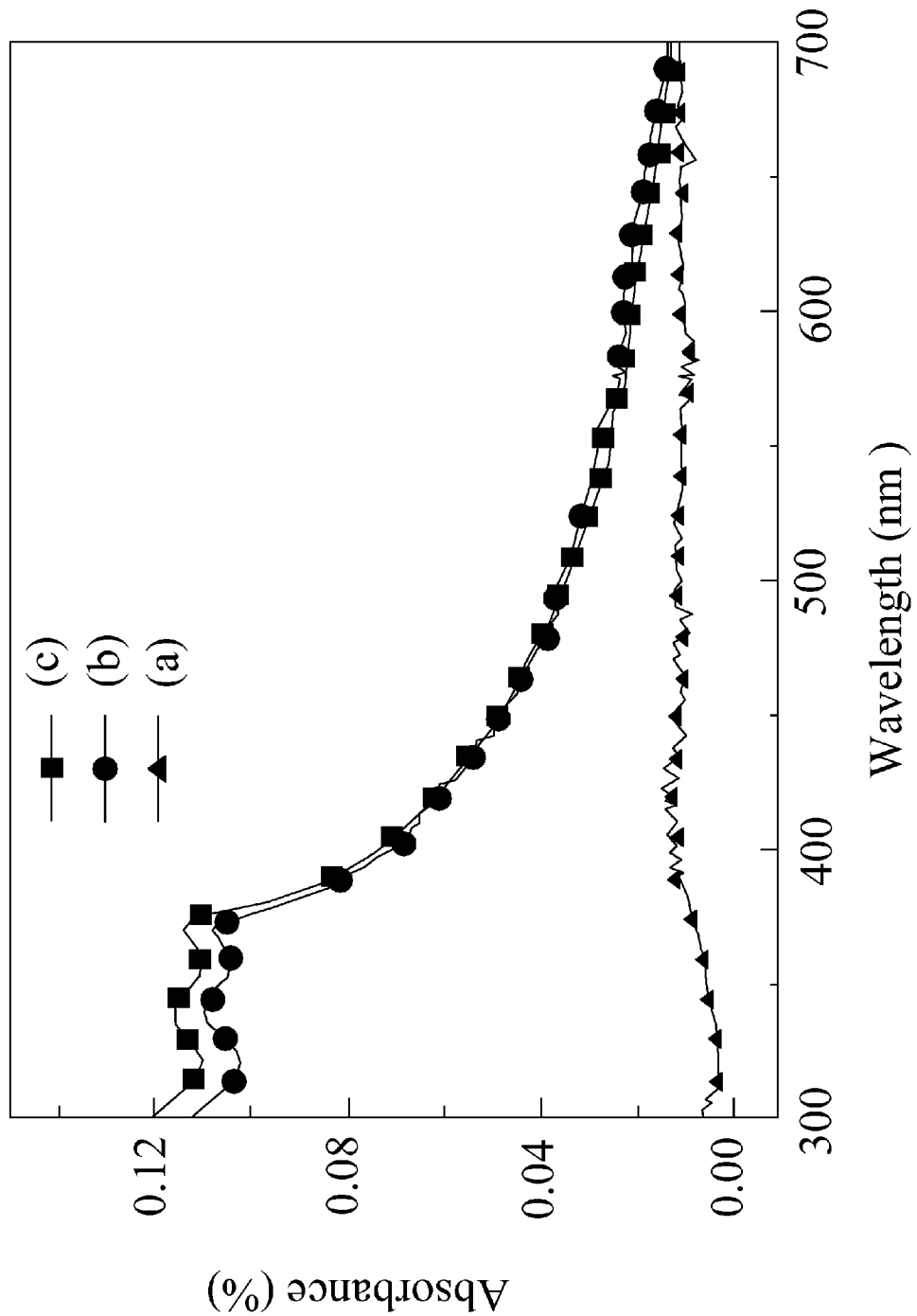
FIG. 6 is an UV-visible absorption spectroscopy of $PC_{61}BSD$ according to the present invention.

Generally, the solvent resistance of the non-cross-linking thin films is not as good as that of the cross-linkable polymer film with a reticular structure. The solvent resistance of the $PC_{61}BSD$ interlayer of the present invention can be proved by using UV-visible absorption spectroscopy, and the results thereof are shown in FIG. 6. In FIG. 6, the $PC_{61}BSD$ interlayer is spuncast from an othro-dichlorobenzene solution and subjected to thermal heating below curing temperature for drying without the thermal curing and then rinsed with a solvent, and the curved (a) thereof shows that the $PC_{61}BSD$ interlayer has the very low absorption. That is, the $PC_{61}BSD$ interlayer without thermal curing is easily washed out by the solvent. However, $PC_{61}BSD$ is subject to thermal curing at an elevated temperature to form the cross-linked $PC_{61}BSD$ interlayer of the present invention and then rinsed by a solvent. The result thereof (curve (b)) is similar as the result of the thin film formed by treating with the thermal curing and without rinsing the solvent (curve (c)). Therefore, in the present invention, the $PC_{61}BSD$ interlayer formed by the thermal cross-linking reaction has solvent resistant property, and can be applicable to manufacturing multilayer organic photovoltaic cells by the solution process.

The above-mentioned results is obtained and explained from the $PC_{61}BSD$ of the present invention. Need for attention, the other formulas of the present invention has the same results, and thus the foregoing results should not be limited implemented scope of the present invention.

Figure 7:
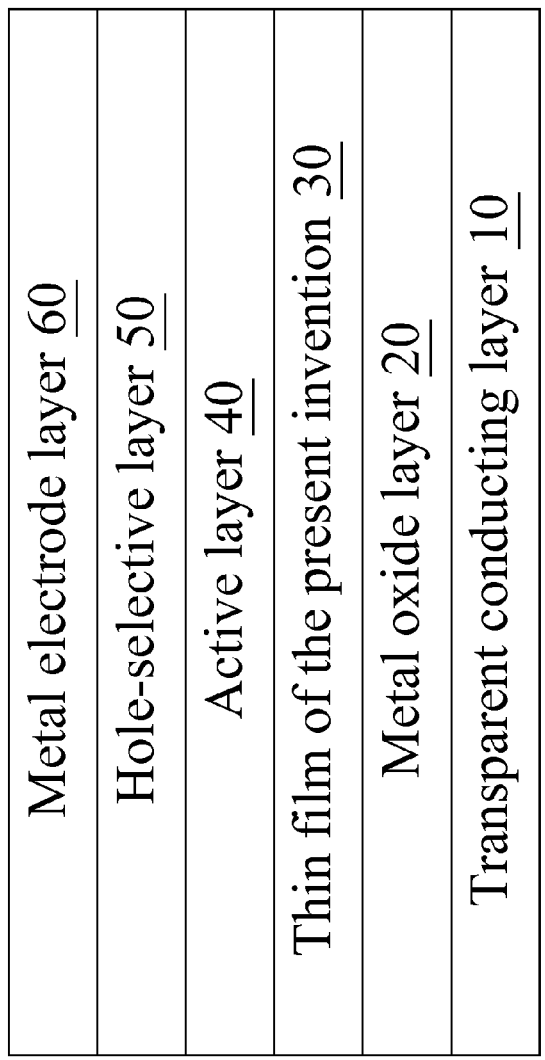
FIG. 7 is a schematic diagram illustrating the structure of an inverted organic photovoltaic cell according to the present invention.

Please refer to FIG. 7, that is a schematic diagram illustrating the structure of an inverted organic photovoltaic cell according to an embodiment of the present invention. As shown, the inverted organic photovoltaic cell of the present invention comprises a transparent conducting layer 10, a metal oxide layer 20, the interlayer 30 of the present invention, an active layer 40, a hole-selective layer 50 and a metal electrode layer 60. In the present embodiment, the metal oxide layer having high visible light transmittance, such as composing of TiOx or ZnO, is formed by the sol-gel process and the high-temperature sintering, and is used as a cathode with the transparent conducting layer 10. The metal electrode layer 60, such as silver (Ag), can be used as an anode of the inverted organic photovoltaic cell. The interlayer 30 of the present invention can capture and transport electrons to the metal oxide layer 20. The active layer 40 can absorb the energy of incident photons to generate excitons. The hole-selective layer 50 captures and transports holes to the metal electrode layer 60.

After heating the polymerizable fullerene derivatives of the present invention, the robust interlayer 30 can be formed. The thickness of the interlayer 30 is about 2-20 nm. The polymerizable fullerene derivatives are covered on the surface of the metal oxide layer 20 by the spin-coating, and then heating (about 140-200° C. to make the cross-linking reaction, such that the interlayer 30 is obtained.

Wherein, the transparent conducting layer 10 may be indium tin oxide (ITO), indium zinc oxide (IZO), aluminum zinc oxide, gallium zinc oxide, aluminum gallium zinc oxide, cadmium tin oxide, zinc oxide (ZnO) or zirconia. The active layer 40 may be a bulk heterojunction (BHJ) layer. The BHJ layer is a polymeric layer, and for example, the BHJ layer may be composed of poly(3-hexylthiophene) (P3HT) and PCBM. The hole-selective layer 50 may be made of poly(3,4-ethylenedioxythiophene) (PEDOT) and poly(styrenesulfonate) (PSS).

The manufacturing method of the inverted organic photovoltaic cell according to an embodiment of the present invention will be described in detail as follows. First, the ITO transparent glass is coated with zinc oxide precursor solution and further processing the soft bake step under 150-250° C. The zinc oxide transparent thin film is formed by the high-temperature calcination at 350-600° C. in air. Additionally, the zinc oxide gel is manufactured through the sol-gel method, that is, the zinc oxide gel is formed via zinc acetate dihydrate and monoethanolamine processing the base-catalytic hydrolysis treatment in anhydrous methanol or anhydrous ethanol. In the reaction, the ratio of zinc acetate dihydrate:monoethanolamine is in a range of 1:0.8 to 1:1.2, and the concentration of zinc acetate dihydrate in anhydrous methanol or anhydrous ethanol is 0.4 M to 1.2 M.

Further, $PC_{61}BSD$ of the present invention is coated on the zinc oxide transparent thin film. $PC_{61}BSD$ is heated to the temperature capable of the thermal cross-linking reaction (about 140-200° C.), such that $PC_{61}BSD$ can be cross-linked under the solid state thereof to obtain the cross-linked $PC_{61}BSD$ (24) interlayer.

Via the contact angle measurement, the $PC_{61}BSD$ interlayer is measured to ensure whether the $PC_{61}BSD$ interlayer is coated on the zinc oxide transparent thin film. The result shows that the contact angle thereof (about 56°) is larger than that of zinc oxide transparent thin film without coating with the $PC_{61}BSD$ interlayer of the present invention (about 28°). Therefore, the result proves that the $PC_{61}BSD$ interlayer is coated on the zinc oxide transparent thin film. After treating by the atomic force microscopy (AFM), the surface of the zinc oxide transparent thin film can be modified effectively by the $PC_{61}BSD$ interlayer of the present invention to decrease the surface roughness, and therefore the efficiency of the inverted organic photovoltaic cell is enhanced.

that the whole efficiency of the inverted organic photovoltaic cells is enhanced over the comparative example.

Figure 8:
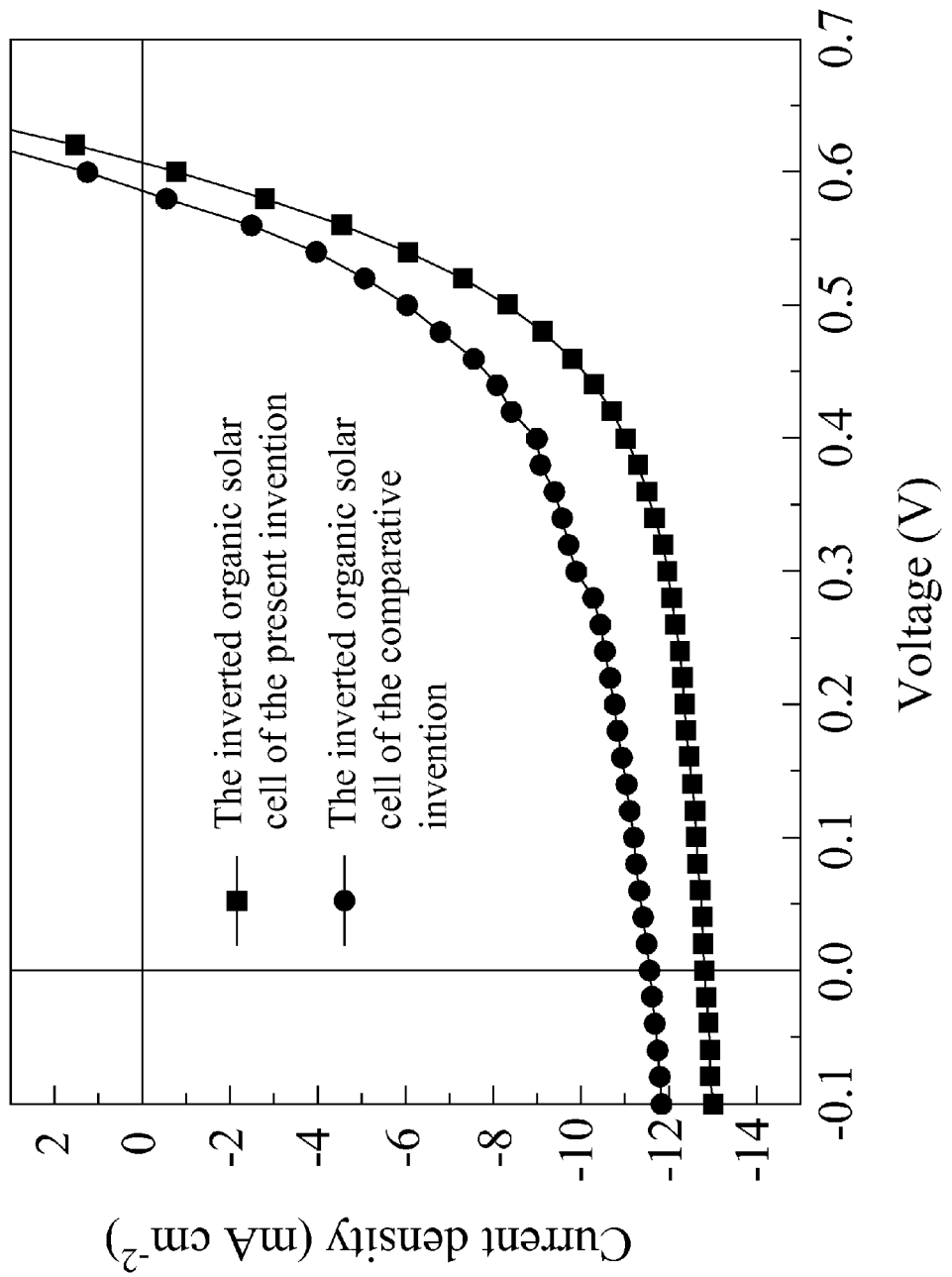
FIG. 8 is a graph illustrating the current density-voltage (J-V) curves between the inverted organic photovoltaic cell of the present invention and the inverted organic photovoltaic cell of the comparative example.
Figure 9:
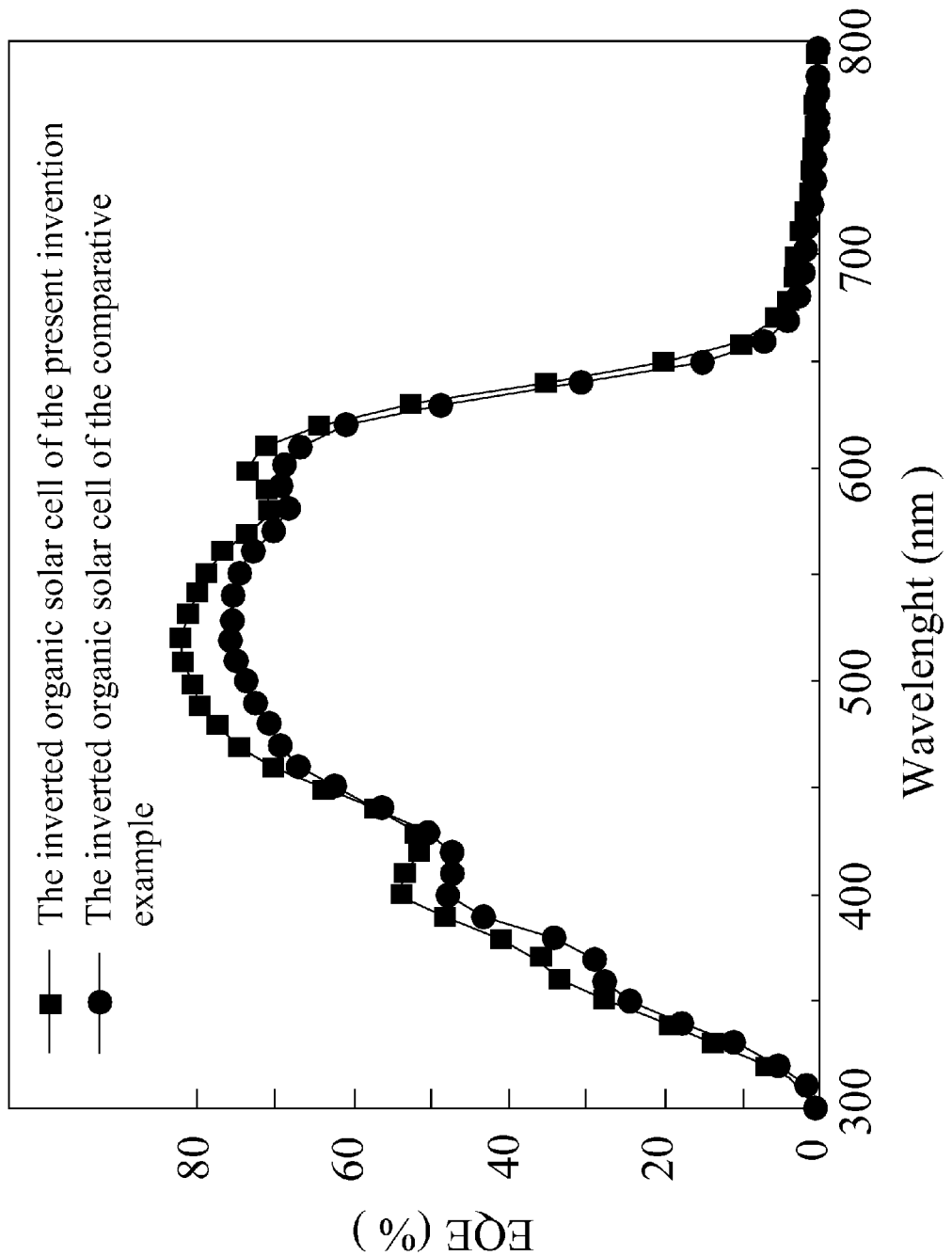
FIG. 9 is a graph illustrating the external quantum efficiency (EQE) between the inverted organic photovoltaic cell of the present invention and the inverted organic photovoltaic cell of the comparative example.
Figure 10:
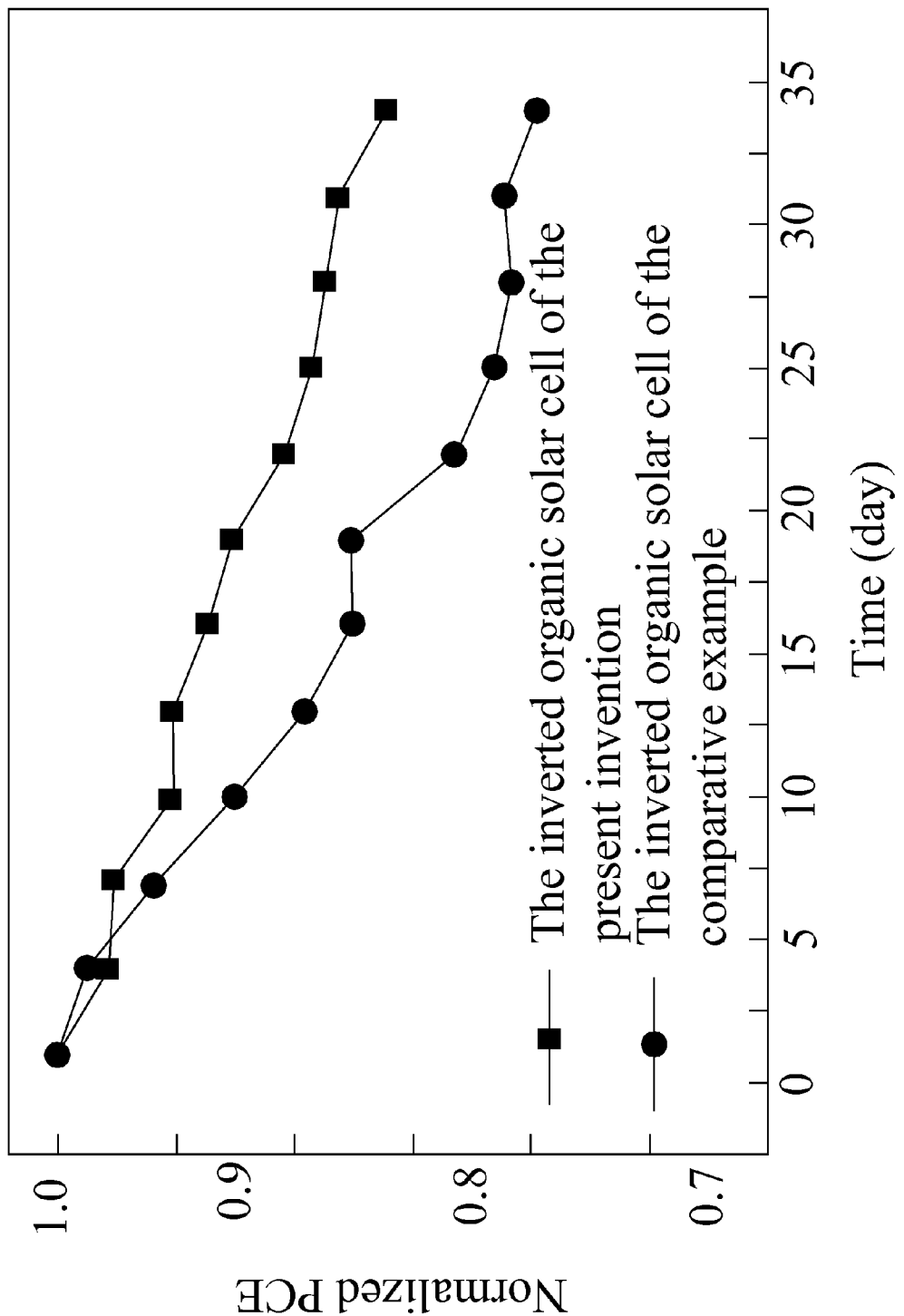
FIG. 10 is a graph illustrating normalized power conversion efficiency-time curves between the inverted organic photovoltaic cell of the present invention and the inverted organic photovoltaic cell of the comparative example.

The difference between the inverted organic photovoltaic cell of the comparative example and that of the present invention is that the inverted organic photovoltaic cell of the comparative example do not have the $PC_{61}BSD$ interlayer of the present invention. The test results are shown in FIG. 8 to FIG. 10, and those respectively are a graph of the current density-voltage (J-V) curves, a graph of external quantum efficiency (EQE) spectra and a graph of normalized power conversion efficiency (PCE)-time curves between the inverted organic photovoltaic cell of the present invention and the inverted organic photovoltaic cell of the comparative example. Please refer to Table 1 simultaneously, which is the detailed photovoltaic parameters between the inverted organic photovoltaic cell of the present invention and the inverted organic photovoltaic cell of the comparative example.

TABLE 1

| Inverted organic photovoltaic cell | $V_{oc}$ (V) | $J_{sc}$ (mA cm$^{-2}$) | FF (%) | η (%) | $R_{sh}$ (W cm$^2$) | $R_s$ (W cm$^2$) |
|---|---|---|---|---|---|---|
| The present invention (with the $PC_{61}BSD$ interlayer) | 0.60 | 12.8 | 58 | 4.4(±0.12) | 553 | 5.9 |
| Comparative example | 0.58 | 11.6 | 52 | 3.5(±0.18) | 292 | 6.2 |

The Table 2 shows the detailed parameters of the electro-optical characteristic between the inverted organic photovoltaic cell, whose active layer is PCPDTBT:$PC_{71}BM$ with the $PC_{61}BSD$ interlayer of the present invention, and the inverted organic photovoltaic cell (without the $PC_{61}BSD$ interlayer) of the comparative example.

TABLE 2

| Inverted organic photovoltaic cell | $V_{oc}$ (V) | $J_{sc}$ (mA cm$^{-2}$) | FF (%) | η (%) | $R_{sh}$ (W cm$^2$) | $R_s$ (W cm$^2$) |
|---|---|---|---|---|---|---|
| The present invention (with the $PC_{61}BSD$ interlayer) | 0.66 | 14.52 | 35 | 3.4(±0.26) | 94 | 10.7 |
| Comparative example | 0.48 | 12.05 | 32 | 1.9(±0.14) | 77 | 10.1 |

After manufacturing the $PC_{61}BSD$ interlayer, P3HT/PCBM, PCPDTBT/PCBM or P3HT/ICBA blend film is covered on top of the $PC_{61}BSD$ interlayer by the spin-coating to form a BHJ layer. The BHJ layer is used as the active layer of the inverted organic photovoltaic cells for absorbing the energy of incident photons to generate excitons (electron-hole pairs).

The PEDOT and PSS solution is spin-coated on the BHJ layer and then drying to form a film as the hole-selective layer of the inverted organic photovoltaic cell for collecting and transporting the holes generated from the active layer to the anode. Preferably, the commercially available Triton X-100 can be added in the PEDOT:PSS aqueous solution, and the proportion thereof is about 0.5-3.0 wt %, thereby increasing the wet ability of PEDOT:PSS aqueous solution to the active layer and firmly adsorbing thereon when spincasting. Finally, a silver electrode is covered on the hole-selective layer, and the silver electrode is formed by thermal vacuum deposition.

After the inverted organic photovoltaic cell of the present invention is manufactured by the above steps, the interlayer, made of the polymerizable fullerene derivatives (either cross-linkable or linearly polymerizable) of the present invention and used as an electron-selective layer of the device, is proved The test results prove that the inverted organic photovoltaic cell can passivate the hotspot and increase the rectification ratio by inserting with the interlayer made of the polymerizable fullerene derivative. Because the inverted organic photovoltaic cell of the present invention has high shunt resistance ($R_{sh}$), the leakage current can be effectively prevented to promote the fill factor (FF), the open-circuit voltage ($V_{oc}$) and the photon-to-current conversion efficiency (η). Additionally, the heterojunction can be formed by inserting the interlayer of the present invention, and thus the active layer can be induced to generate the lateral microphase separation and rule out the disadvantage of the electric field built in blending system, thereby effectively increasing the short-circuit current ($J_{sc}$) and the external quantum efficiency as shown in FIG. 8 and FIG. 9. Furthermore, FIG. 10 shows that the life cycle of the inverted organic photovoltaic cell with the $PC_{61}BSD$ interlayer of the present invention is better than that of the comparative example.

In another embodiment, the active layer of the organic photovoltaic cell can be formed by ICBA and P3HT, and the PC61BSD interlayer can be disposed between a metal oxide layer and an active layer. That is, the structure of the organic photovoltaic cell according to the present invention is ITO/

Figure 11:
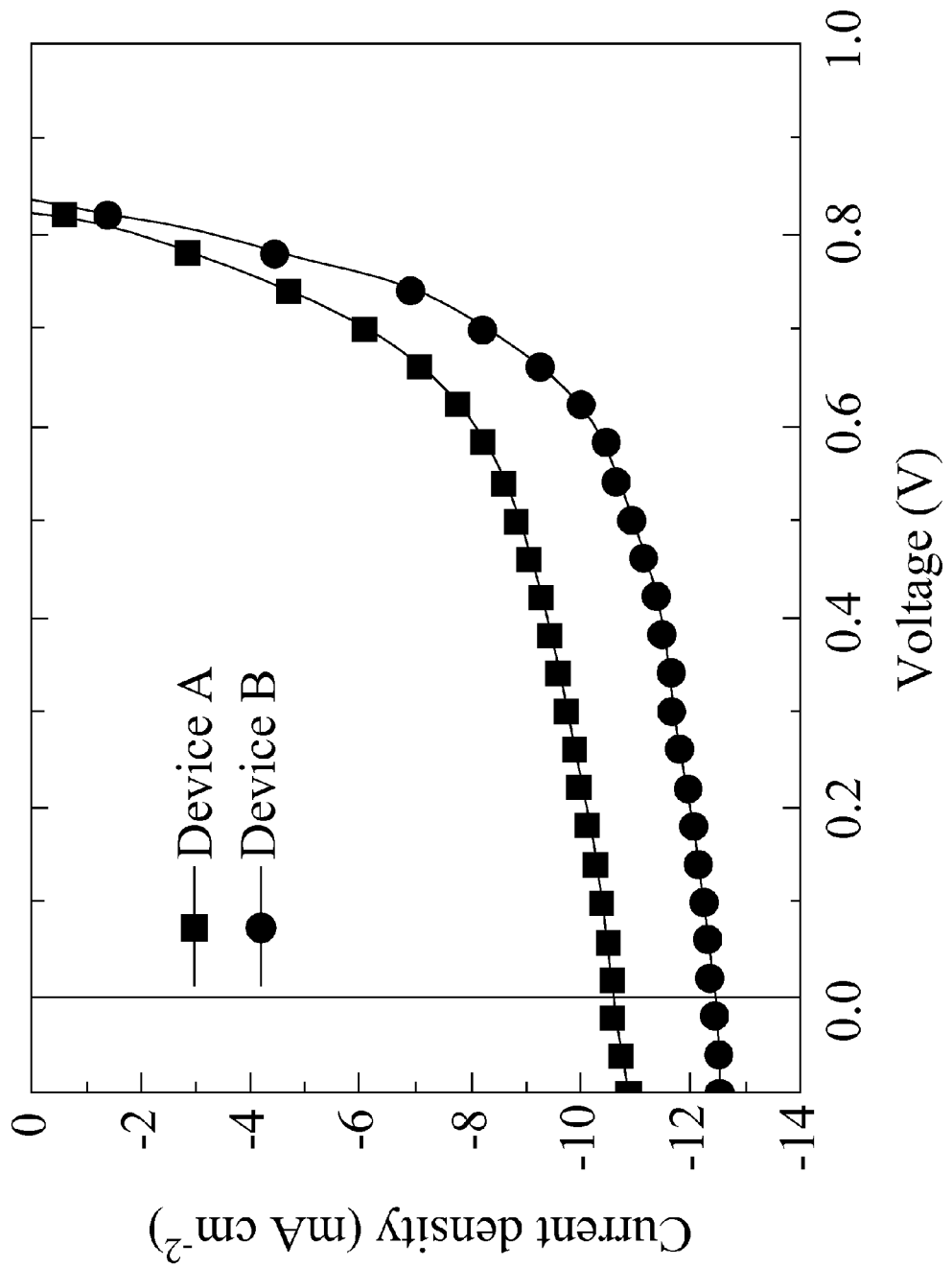
FIG. 11 is a graph illustrating the current density-voltage (J-V) curves between the device B of the present invention and the device A of the comparative example.
Figure 12:
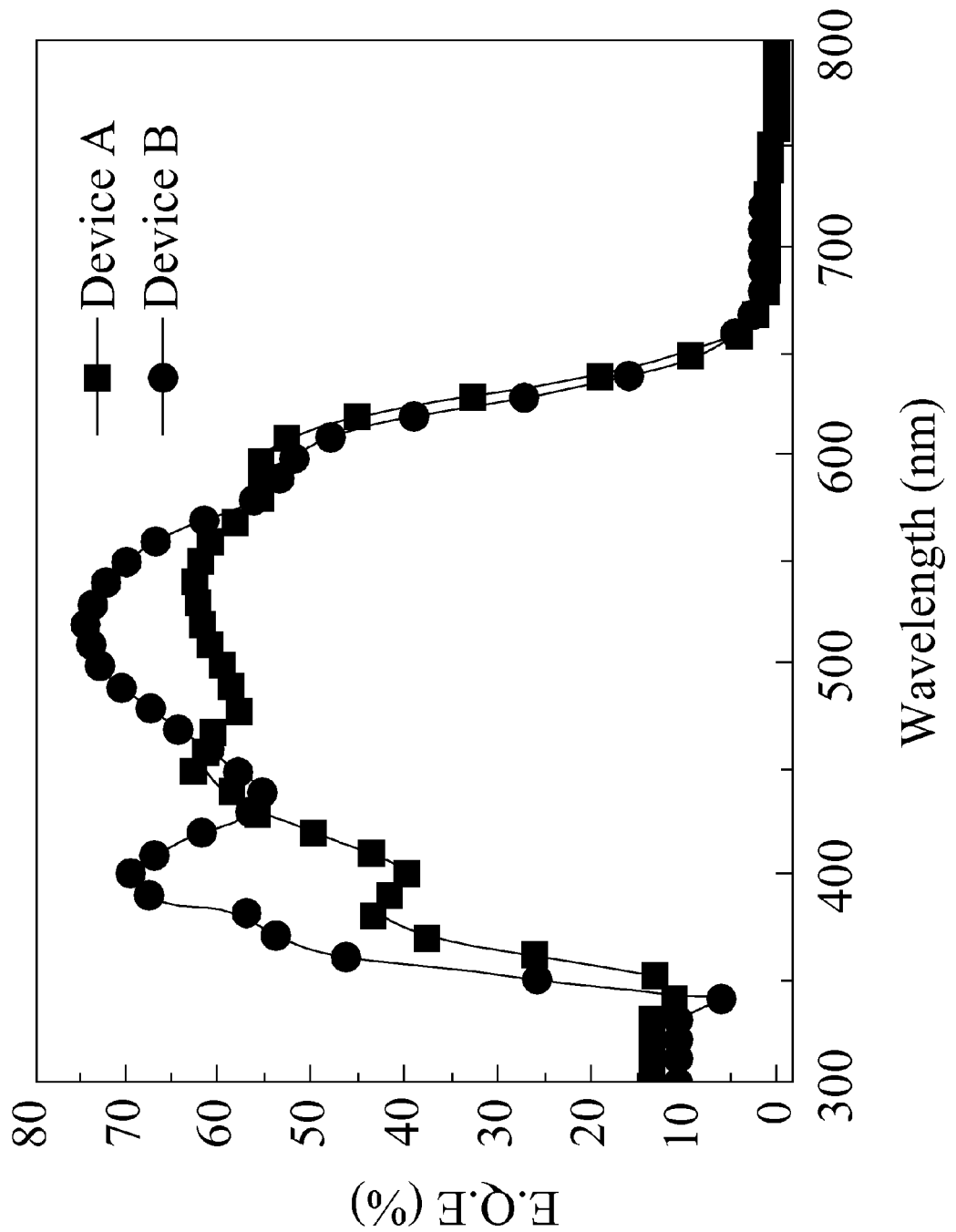
FIG. 12 is a graph illustrating the EQE between the device B of the present invention and the device A of the comparative example.

ZnO/PC$_{61}$BSD/ICBA:P3HT (1:1, w/w)/PEDOT:PSS/Ag, which hereinafter referred to as "device B". Compared to the device A, which is ITO/ZnO/ICBA:P3HT (1:1, w/w)/PEDOT:PSS/Ag, the device B exhibits an enhanced V$_{oc}$=0.84 V, J$_{sc}$=12.4 mA/cm$^2$, and FF=60%, achieving an exceptional PCE of 6.22% which is a 29% increase over device A (FIG. 11). Device B also had a large EQE maximum of 74%, which is concordant with its high photocurrent (FIG. 12). More importantly, the high performance of device B is reproducible. Furthermore, since ICBA is the major component in the active layer making contact with the bottom layer, the localized ICBA/PC$_{61}$BSD interface in the device B plays a dominant role in determining the electron-extracting properties. Unlike the organic-inorganic ICBA/ZnO interface in device A, the fullerene-based organic-organic ICBA/PC$_{61}$BSD interface with intimate contact in device B enhances electrical coupling and lowers contact resistance. This facilitates electron transport and thereby reduces charge recombination losses at the interface. The higher LUMO energy level of ICBA is also beneficial in terms of energy alignment at the interface. The PC$_{61}$BSD LUMO energy level (−3.91 eV) is located between the LUMO of ICBA (−3.74 eV) and the conduction band of ZnO (−4.4 eV). Therefore, PC$_{61}$BSD functions as an intermediate in an energy gradient, such that electrons in the ICBA domain can be efficiently extracted by PC$_{61}$BSD and transported to the ZnO through an energetically favorable pathway.

Even though the foregoing results shows the test results of the polymerizable fullerene derivative formed by the thermally polymerizable functional group, the polymerizable fullerene derivatives formed by the photochemically polymerizable functional group have the test results and advantages. Therefore, via inserting the interlayer of the present invention in the inverted organic photovoltaic cells to use as an electron-selective layer, high solvent resistance can be achieved during the wet etching process, and the interlayer of the present invention has excellent ability to capture and transport electrons.

Accordingly, in the inverted organic photovoltaic cells, the heterojuction can be formed by the interlayer of the present invention and electron donor of the active layer so as to increase the exciton dissociation efficiency. Furthermore, the interlayer formed by the polymerizable fullerene derivatives of the present invention can provide the nucleation point of the electron acceptor at the bulk heterojunction active layer to induce that the active layer generates the effective lateral microphase separation and simultaneously increase the crystallinity of electron donors. The interlayer of the present invention can effectively enhance the ability of capturing electrons and blocking holes to decrease the leakage current, such that the object of increasing the photoelectric conversion efficiency of the inverted organic photovoltaic cells is achieved by means of all solution process.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A polymerizable fullerene derivative, represented by any one of following formulae:

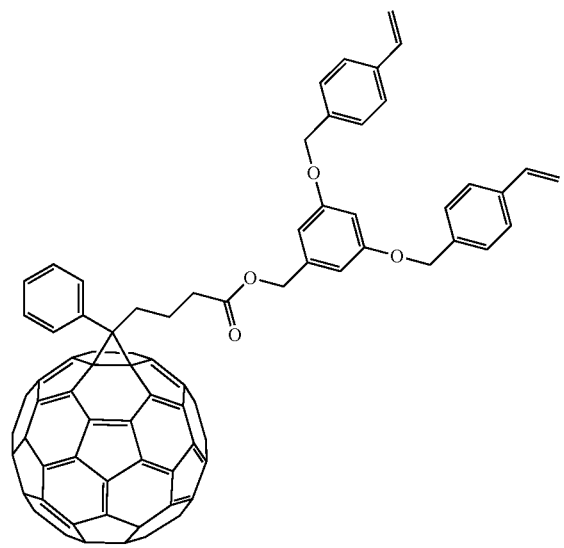
(1)

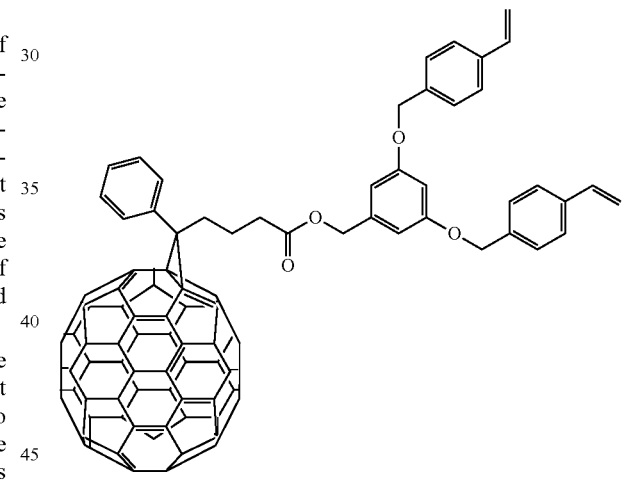
(2)

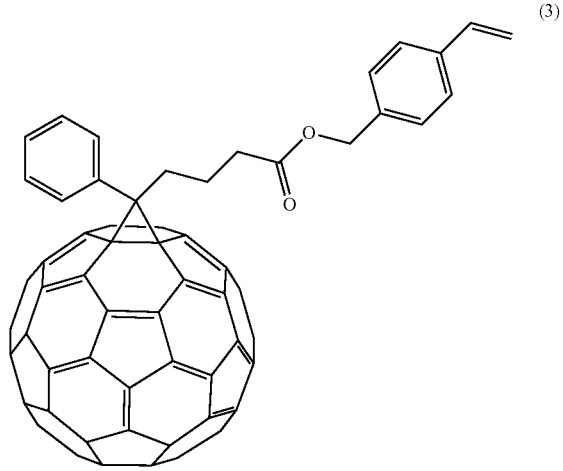
(3)

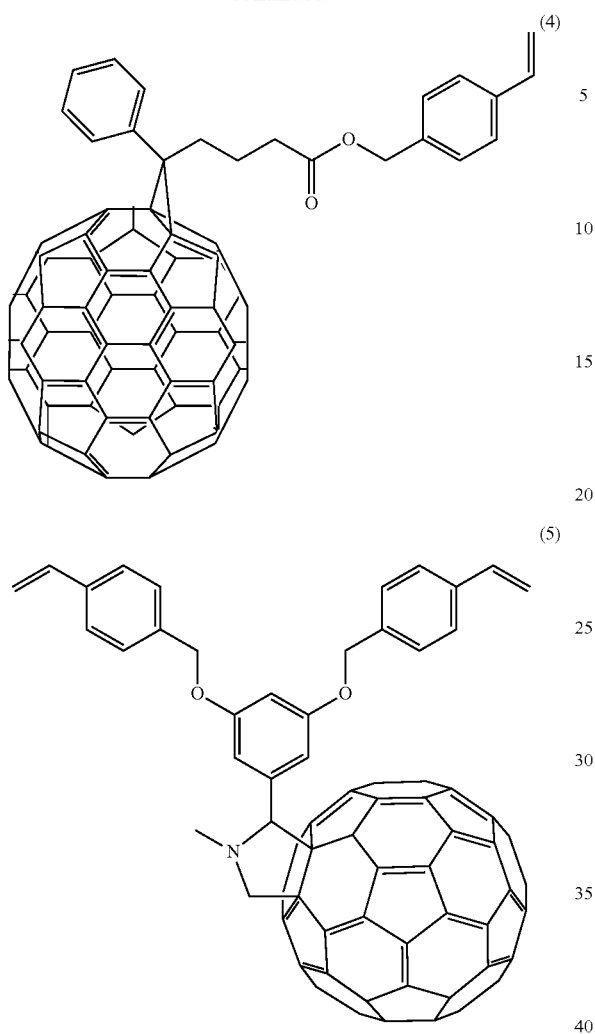
(4)
(5)
(6)
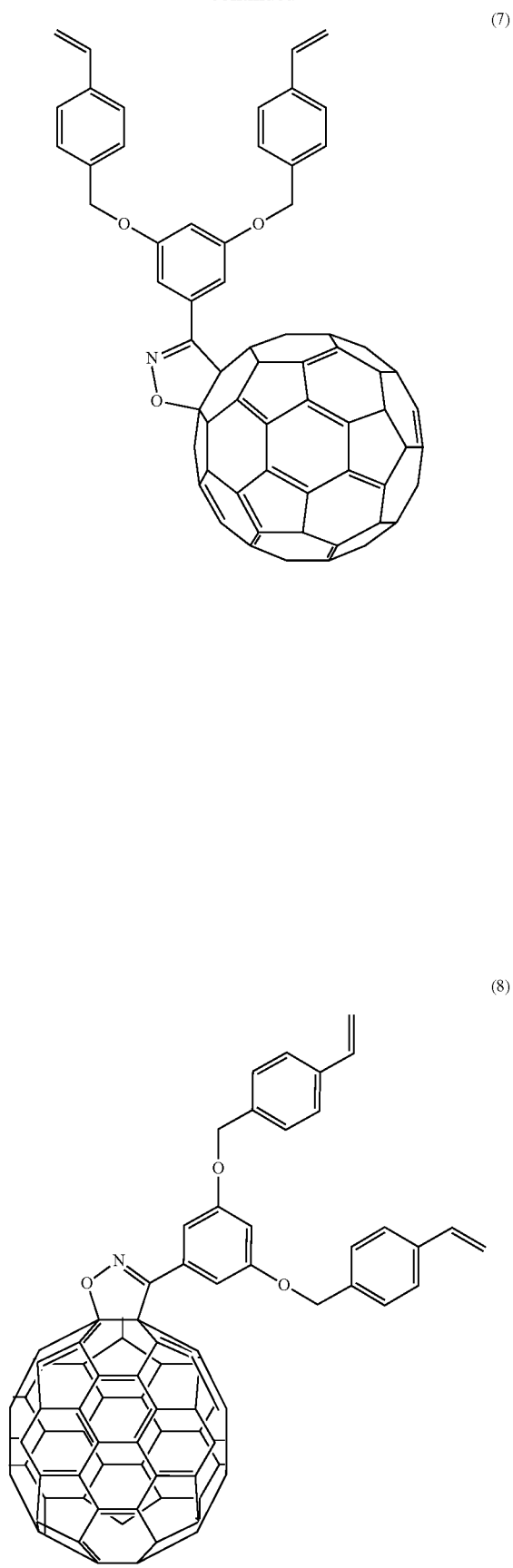
(7)
(8)

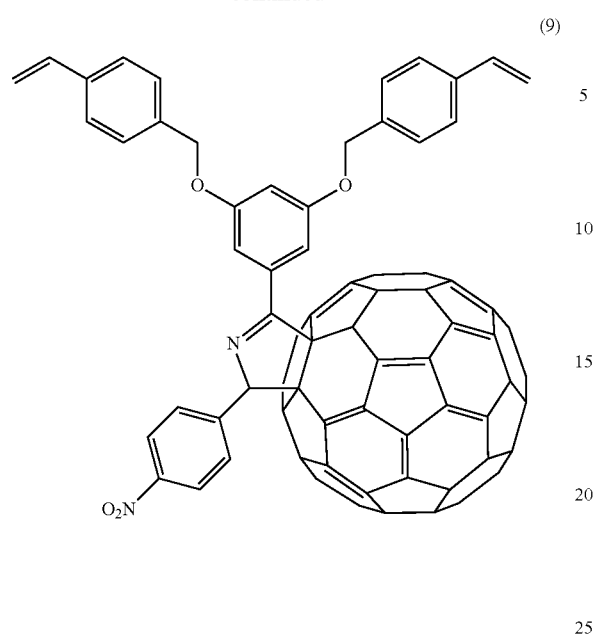
(9)
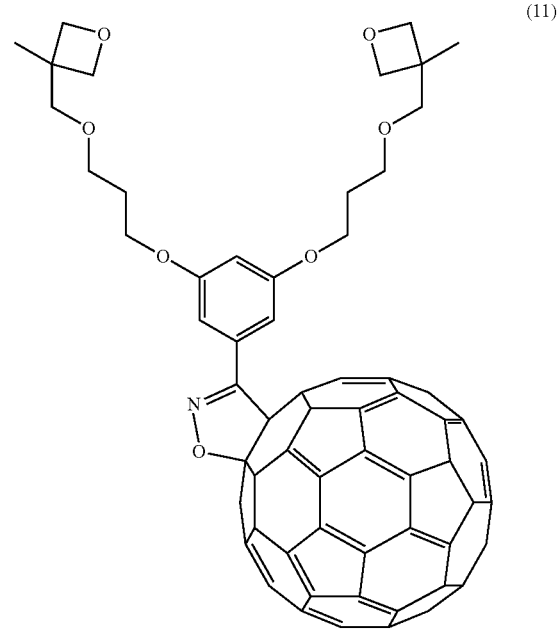
(11)
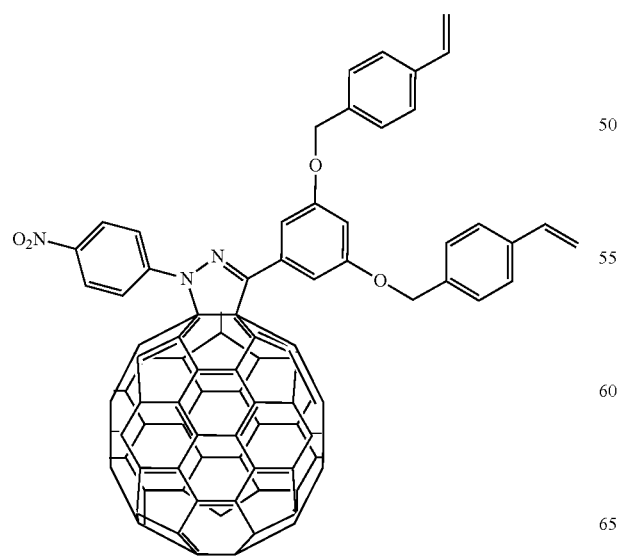
(10)
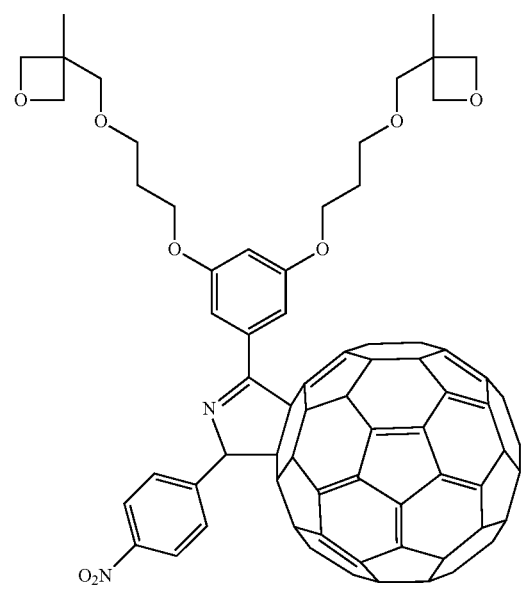
(12)

(13)
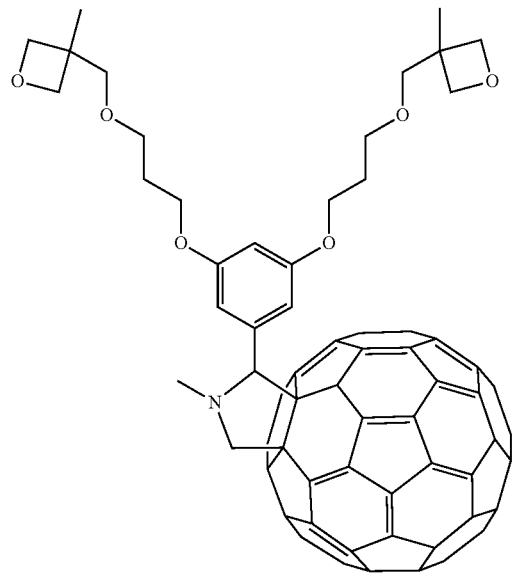
(15)
(14)
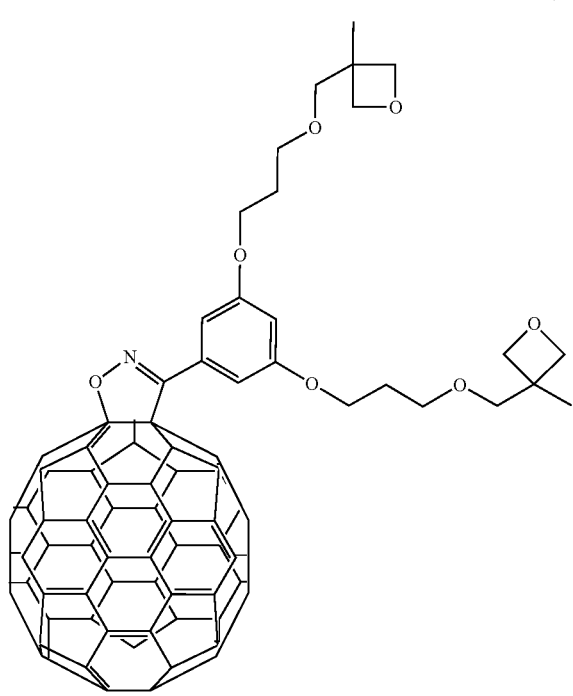
(16)
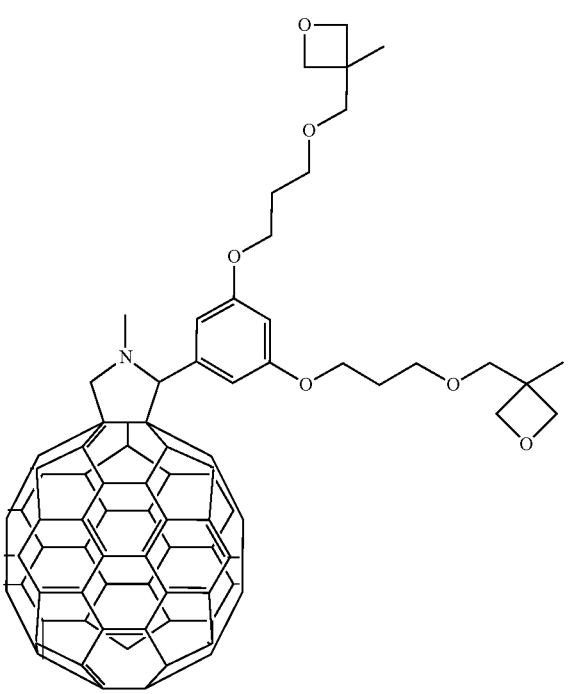

(17)
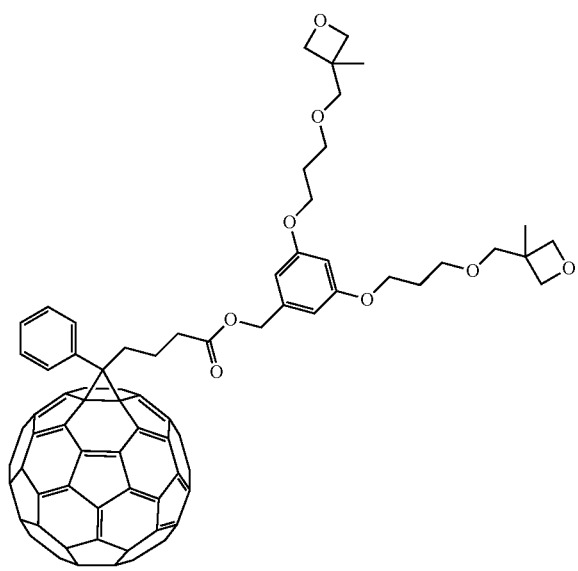
(18)
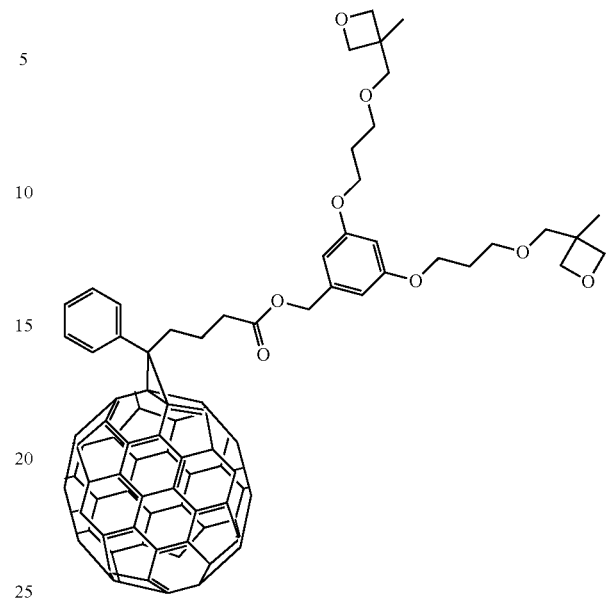
wherein the fullerene structures shown in formulae 1, 3, 5, 7, 9, 11-13, and 17 are $C_{60}$ structures and the fullerene structures shown in formulae 2, 4, 6, 8, 10, 14-16, and 18 are $C_{70}$ structures.
2. An inverted organic photovoltaic cell, comprising:
an interlayer made of the polymerizable fullerene derivative as claimed in claim 1, and disposed between a metal oxide layer and an active layer.
* * * * *